United States Patent
Stobbe

(10) Patent No.: US 10,288,060 B2
(45) Date of Patent: May 14, 2019

(54) ELECTRONICALLY CONTROLLED DIAPHRAGM PUMP

(71) Applicant: STOBBE PHARMA TECH GMBH, Chiasso (CH)

(72) Inventor: Per Stobbe, Holte (DK)

(73) Assignee: STOBBE PHARMA TECH GMBH, Chiasso (CH)

( * ) Notice: Subject to any disclaimer, the term of this patent is extended or adjusted under 35 U.S.C. 154(b) by 0 days.

(21) Appl. No.: 14/945,219

(22) Filed: Nov. 18, 2015

(65) Prior Publication Data

US 2016/0195081 A1    Jul. 7, 2016

Related U.S. Application Data

(63) Continuation of application No. 13/125,900, filed as application No. PCT/DK2009/000261 on Dec. 18, 2009, now abandoned.

(30) Foreign Application Priority Data

Dec. 19, 2008 (DK) ................................ 2008 01815
Oct. 19, 2009 (DK) ................................ 2009 01131
(Continued)

(51) Int. Cl.
*F04B 43/00* (2006.01)
*F04B 43/073* (2006.01)
(Continued)

(52) U.S. Cl.
CPC ............. *F04B 49/06* (2013.01); *C12M 29/00* (2013.01); *F04B 43/0081* (2013.01);
(Continued)

(58) Field of Classification Search
CPC ........ F04B 43/02; F04B 43/06; F04B 43/073; F04B 43/0736; F04B 45/04; F04B 45/053; F04B 45/0536; C12M 29/00; C12M 29/14
(Continued)

(56) References Cited

U.S. PATENT DOCUMENTS 3,551,076 A    12/1970    Wilson
3,554,672 A     1/1971    Brandes
(Continued)

FOREIGN PATENT DOCUMENTS

AU    5532986 A    10/1987
DE    19826610 A    12/1999
(Continued)

OTHER PUBLICATIONS

Furey, "Bioprocess Tutorial Continuous Cell Tulture Using the ATF System", Genetic Engineering News, vol. 20, No. 10, (May 15, 2000), pp. 52-56.
(Continued)

*Primary Examiner* — Peter J Bertheaud
(74) *Attorney, Agent, or Firm* — Maier & Maier, PLLC

(57) ABSTRACT

An electronically controlled diaphragm pump system includes a pump housing with a drive gas chamber, a fluid chamber separated by a diaphragm, gas pressure means for providing a drive gas pressure in response to a control signal, and gas under-pressure means connected to a gas outlet port for providing a gas outlet under-pressure or sucking of gas in response to a control signal. The pump system has a displacement sensor and control circuitry connected to the displacement sensor for determining the displacement or position of the diaphragm and adapted or supplying the control signals to the gas pressure means and the gas under-pressure means.

9 Claims, 10 Drawing Sheets

(30) Foreign Application Priority Data

Oct. 21, 2009 (DK) .............................. 2009 01142
Oct. 29, 2009 (DK) .............................. 2009 01165

(51) Int. Cl.

| | | |
|---|---|---|
| F04B 45/053 | (2006.01) | |
| F04B 49/06 | (2006.01) | |
| C12M 1/00 | (2006.01) | |
| F04B 49/08 | (2006.01) | |
| C12M 3/00 | (2006.01) | |
| C12M 1/12 | (2006.01) | |

(52) U.S. Cl.
CPC ........ *F04B 43/073* (2013.01); *F04B 43/0733* (2013.01); *F04B 43/0736* (2013.01); *F04B 45/053* (2013.01); *F04B 45/0536* (2013.01); *F04B 49/08* (2013.01); *C12M 23/34* (2013.01); *C12M 23/42* (2013.01); *C12M 25/14* (2013.01)

(58) Field of Classification Search
USPC .................... 417/383, 384, 393, 394, 395
See application file for complete search history.

(56) References Cited

U.S. PATENT DOCUMENTS

| | | | |
|---|---|---|---|
| 3,568,214 A | 3/1971 | Goldscmeid | |
| 3,704,965 A | 12/1972 | Mentschel | |
| 4,201,845 A | 5/1980 | Feder | |
| 4,452,572 A | 6/1984 | Evrard | |
| 4,494,912 A | 1/1985 | Pauliukonis | |
| 4,514,499 A | 4/1985 | Noll | |
| 4,546,083 A | 10/1985 | Meyers | |
| 4,789,634 A | 12/1988 | Muller | |
| 4,937,196 A | 6/1990 | Wrasidlo | |
| 4,948,728 A | 8/1990 | Stephanopoulos | |
| 4,978,616 A | 12/1990 | Dean | |
| 5,002,471 A | 3/1991 | Perlov | |
| 5,190,878 A | 3/1993 | Wilhelm | |
| 5,249,932 A | 10/1993 | Bork | |
| 5,252,041 A * | 10/1993 | Schumack | F04B 43/073 417/395 |
| 5,257,914 A * | 11/1993 | Reynolds | F04B 43/067 417/293 |
| 5,266,476 A | 11/1993 | Sussman | |
| 5,362,622 A | 11/1994 | O'Dell | |
| 5,378,122 A | 1/1995 | Duncan | |
| 5,501,971 A | 3/1996 | Freedman | |
| 5,543,047 A | 8/1996 | Stoyell | |
| 5,563,069 A | 10/1996 | Yang | |
| 6,126,403 A * | 10/2000 | Yamada | F04B 43/0081 417/395 |
| 6,544,424 B1 | 4/2003 | Sevitz | |
| 6,554,578 B1 | 4/2003 | Siegel | |
| 6,796,215 B1 | 9/2004 | Hauser | |
| 6,844,187 B1 | 1/2005 | Wechsler | |
| 6,948,918 B2 | 9/2005 | Hansen | |
| 7,717,682 B2 | 5/2010 | Orr | |
| 8,038,640 B2 | 10/2011 | Orr | |
| 8,197,231 B2 | 6/2012 | Orr | |
| 9,228,579 B2 | 1/2016 | Stobbe | |
| 2002/0034447 A1 | 3/2002 | Brazil | |
| 2004/0048366 A1 | 3/2004 | Stroh | |
| 2004/0132175 A1 | 7/2004 | Vetillard | |
| 2004/0136843 A1 | 7/2004 | Jahn | |
| 2005/0158851 A1 | 7/2005 | Furey | |
| 2006/0115894 A1 | 6/2006 | Wan | |
| 2007/0077156 A1 | 4/2007 | Orr | |
| 2007/0177998 A1 | 8/2007 | Kato | |
| 2008/0003676 A1 | 1/2008 | Sheridan | |
| 2008/0131957 A1 | 6/2008 | Ryan | |
| 2008/0175825 A1 | 7/2008 | Hampson | |
| 2008/0248552 A1 | 10/2008 | Castillo Fernandez | |
| 2009/0047137 A1 | 2/2009 | Stenberg | |
| 2009/0068032 A1 | 3/2009 | Furey | |
| 2009/0176301 A1 | 7/2009 | Oldenburg | |
| 2009/0311776 A1 | 12/2009 | Kelly | |
| 2010/0075405 A1 | 3/2010 | Broadley | |
| 2011/0223581 A1 | 9/2011 | Stobbe | |
| 2011/0236932 A1 | 9/2011 | Stobbe | |

FOREIGN PATENT DOCUMENTS

| | | |
|---|---|---|
| EP | 155237 A2 | 9/1985 |
| EP | 317874 A2 | 5/1989 |
| EP | 498565 A | 8/1992 |
| EP | 0498565 A1 | 8/1992 |
| EP | 2379889 B | 9/2015 |
| WO | 2000015962 | 3/2000 |
| WO | 2005118771 A1 | 12/2005 |
| WO | 2007039600 A1 | 4/2007 |
| WO | 2007142664 A1 | 12/2007 |
| WO | 2009069960 A2 | 6/2009 |
| WO | 2010069321 | 6/2010 |

OTHER PUBLICATIONS

Furey, "Bioprocessing application note, Scale-up of a Cell Culture Perfusion Process", Genetic Engineering News, vol. 22, No. 7, (Apr. 1, 2002), pp. 62-63.
Tube-O-Matic, "How ii Works", Lexair, Inc. (2004).
Hygienic Solutions, The Evolution of Clean, Wilden (2006).
Refine Technology, ATF System, Designed to Improve your Bioprocess, pp. 1-4 (2007).
U.S. Appl. No. 13/125,900 (parent of instant appln and published as 2011/0223581), Office Action dated Feb. 3, 2014.
U.S. Appl. No. 13/125,900 (parent of instant appln and published as 2011/0223581), Final Office Action dated Sep. 16, 2014.
U.S. Appl. No. 13/125,900 (parent of instant appln and published as 2011/0223581), Non-Final Office Action dated Jan. 6, 2015.
U.S. Appl. No. 13/125,900 (parent of instant appln and published as 2011/0223581), Office Action dated Aug. 19, 2015.
WO Appln. No. PCT/DK2009/000261 (published as WO2010069321 and counterpart to U.S. Appl. No. 13/125,900), International Search Report, dated Jul. 23, 2010.
WO Appln. No. PCT/DK2009/000261 (published as WO2010069321 and counterpart to U.S. Appl. No. 13/125,900), IPRP, dated Jun. 13, 2011.
EP09805912 (published as EP2379889 and counterpart to U.S. Appl. No. 13/125,900), Applicant Communication, dated Jul. 13, 2011.
EP09805912 (published as EP2379889 and counterpart to U.S. Appl. No. 13/125,900), EP Office Communication, dated Mar. 1, 2013.
EP09805912 (published as EP2379889 and counterpart to U.S. Appl. No. 13/125,900), response to EP Office Communication, dated Aug. 28, 2013.
EP09805912 (published as EP2379889 and counterpart to U.S. Appl. No. 13/125,900), EP Office Communication, dated Oct. 10, 2014.
EP09805912 (published as EP2379889 and counterpart to U.S. Appl. No. 13/125,900), response to EP Office Communication, dated Dec. 11, 2014.
EP09805912 (published as EP2379889 and counterpart to U.S. Appl. No. 13/125,900), response intention to grant patent, dated Apr. 28, 2015.
Applegate et al. (1992) "Development of a Single-Pass Ceramic Matrix Bioreactor for Large-Scale Mammalian Cell Culture", Biotechnology and Bioengineering 40:1056-1068.
Brunelle (1978) "Preparation of Catalysts by Metallic Complex Adsorption of Mineral Oxides", Pure & Appl. Chem 50:1211-1229.
Cell Culture Bioreactors, (Aug. 2011), pp. 1-23.
Cellular Bioprocess Technology (2004), University of Minnesota, pp. 18-24.
Chen et al. (2002) "A Fibrous-bed bioreactor for continuous production of developmental endothelial locus-1 by osteosarcoma cells", Journal of Biotechnology 97:23-39.

(56) References Cited

OTHER PUBLICATIONS

Chiou et al. (1991). "A Fiber-Bed Bioreactor for Anchorage-Dependent Animal Cell Cultures: Part I. Bioreactor Design and Operations", Biotechnology and Bioengineering 37:755-761.
Fassnacht et al. (1998) "Long-term cultivation of immortalised mouse hepatocytes in a high cell density, fixed-bed reactor", Biotechnology Techniques 12: 25-30.
Lameiras et al. (2008) "Measurement of the Zeta Potential of Planar Surfaces With a Rotating Disk", Mat. Res. 11:217-219.
Lee et al., (2005) "Recombinant Antibody Production by Perfusion Cultures of rCHO Cells in a Depth Filter Perfusion System," Biotechnol. Prog., 21:134-139.
Lewis (2000) "Colloidal Processing of Ceramics", J. Am. Ceram. Soc., 83 :2341-59.
Li et al. (2009) "A single use, scalable perfusion bioreactor system" Bioprocess International/Supplement, 1 , pp. 46-54.
Lokhande et al. (1984) "Grafting onto polyester fibres", Colloid & Polymer Science 262: pp. 127-130.
Meuwly et al., (2007) "Packed-bed bioreactors for mammalian cell culture: Bioprocess and biomedical applications", Biotechnology Advances 25 :45-56.
Murakami et al. (1991) "A Fiber-Bed Bioreactor for Anchorage-Dependent Animal Cell Cultures: Part II. Scaleup Potential", Biotechnology and Bioengineering 37: 762-769.
Oh et al. (1994) "High-Density Continuous Cultures of Hybridoma Cells in a Depth Filter Perfusion System", Biotechnology and Bioengineering 44: 895-901.
Turick et al. (1993) "Review of Nonconventional Bioreactor Technology", Idaho National Engineering Laboratory.
Wang et al., (1992)."Modified CelliGen-packed bed bioreactors for hybridoma cell cultures", Cytotechnology 9:41-49.

\* cited by examiner

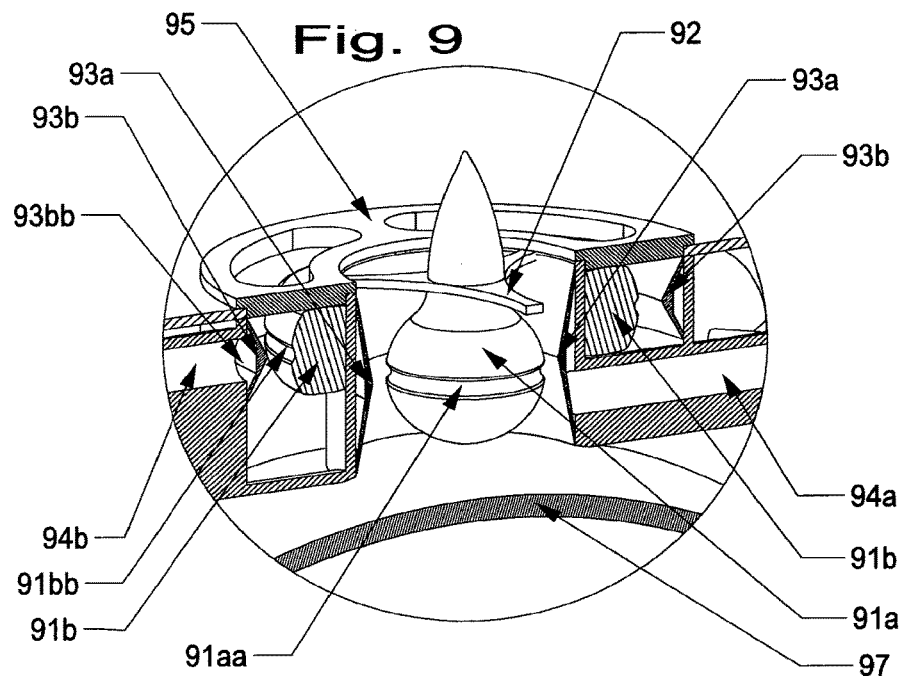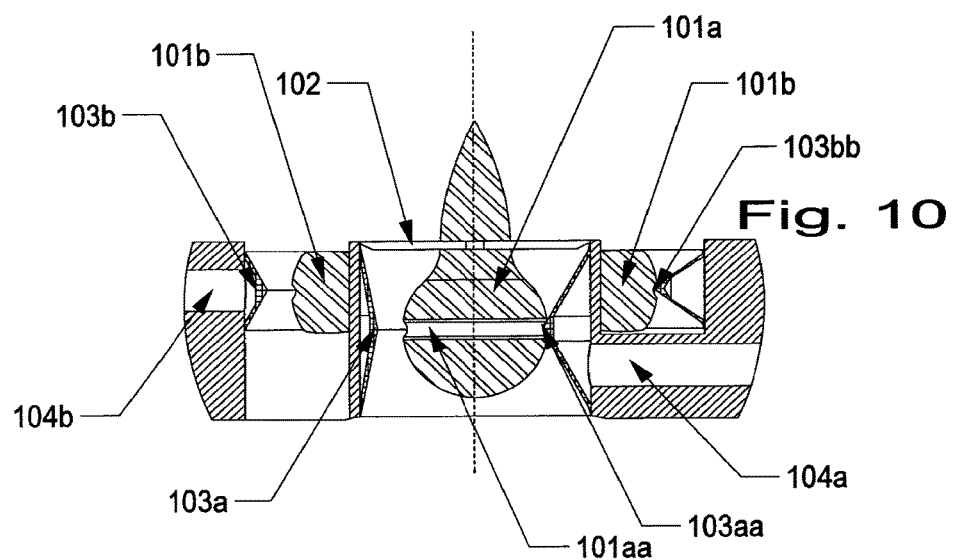

ELECTRONICALLY CONTROLLED DIAPHRAGM PUMP

TECHNICAL FIELD

The present invention relates to a diaphragm pump, which may be fully electronically controlled and driven by pneumatics. The pump may be suitable for circulation of critical fluids in the chemical or pharmaceutical industry, and parts of the pump having media or fluid contact may be manufactured from disposable materials.

BACKGROUND OF THE INVENTION

The disposable bioreactors were considered a novelty, and perhaps even a passing trend, as recently as mid 90ties. As single-use bioreactors have matured and begun to address most of these issues, their market acceptance has rapidly expanded. The move to disposable bioreactors is, in many instances, driven by reduction in sterilisation and cleaning requirements, improved plant flexibility, reduced costs and faster time to market for the end product. All of these benefits have been recently documented. These hurdles include the ability to add reliable, accurate, low cost sensors and pumping devices so that standards can be generated and the process repeatability readily documented.

The New Brunswick Scientific in the US and other manufactures stirred-tank bioreactor systems circulates the nutrient internally by a rotating centrifugal pump head submersed into the nutrient. The mechanical shaft connects the impeller to an electrical motor placed outside on top of the bioreactor. ATMI-Life Science, Artelis both in Belgium, Sartorius-Stedim in Germany, LevTech in the US and other suppliers of disposable plastic bags includes a mixing device inside at the disposable plastic bag bottom. Magnetic forces transfer the rotating force from an external mounted drive arrangement eliminating rotating axles penetrating the bag wall. As there is always a magnet in the rotating device, it is not a fully disposable pump system.

The use of tube pumps, peristaltic pumps like from US company Watson Marlow is the closest one gets to single-use pumps in the pharmaceutical industry with limited mass transfer capacity. Further the typical peristaltic pump of reasonable capacity is very expensive. No manufacturer offers a 100% single-use, disposable diaphragm pump for low energy consumption during operation at low initial cost.

Traditional diaphragm pumps are typically twin-membrane pneumatic operated and free-wheeling with no media to pump or changes in media viscosity. No pumps are known with electronic control of operation, such as variable stroke, variable strokes frequency independent of pumped media viscosity or ability to handle more than one fluid circuit. No disposable, electronically controlled diaphragm pump is available from important suppliers such as German DEPA/Crane, US based Wilden, Trebor or Swedish companies like Kelva and Dominator.

A diaphragm pump is a positive displacement pump that typically uses a combination of the reciprocating action of a rubber, thermoplastic, elastomeric or even Teflon diaphragm and suitable non-return check valves to pump a fluid. Sometimes this type of pump is also called a membrane pump. When the volume of a chamber is increased (the diaphragm moving), the pressure on the inlet valve(s) decreases, and fluid is drawn into the chamber. When the chamber pressure later increases from decreased volume (the diaphragm moving), the fluid previously drawn in is discharged through the exhaust valve(s). Finally, the diaphragm moving once again draws fluid into the chamber, completing the reciprocating cycle. The pump principle offers gently conveyance of liquids and is ideal for a sensitive media. The known diaphragm pumps have no measures built in for tracking the actual volume being pumped and are further depending on on/off valves with no one taking advantage of proportional valves for membrane position regulation.

Within the pharmaceutical, chemical and dairy industry, the diaphragm pump has been used intensively for hundred years or more in a variety of configurations. Though all diaphragm pumps are of non-integrated, independent design and open installation, they all demand regular maintenance in long time use in aggressive or particle filled media. The pump body is often manufactured from cast steel, stainless steel and expensive Teflon and typically the membranes are manufactured from silicone, EPDM, Teflon or the like of flexible materials.

Definitions Relevant for the Present Invention

Bioreactor or fermenter—a physical device, a container, a vessel which support biologically active environment and houses micro organism performing a process Bag—a flexible container made from clear plastic foil also used as bioreactor vessel Single-use—products intended for one time use only Disposable—products manufactured from organic materials and at low cost Leachables—Chemical compounds that migrate from product contact when exposed to an appropriate solvent Extractables—Chemical compounds, typically a subset of extractables, that migrate into the fluid from direct contact Diaphragm pump—traditionally a non-disposable pneumatics operated twin membrane, twin housing pump with the flexible membrane element in contact with the media Peristaltic pump—a pump with the element in contact with the media being a single-use, replaceable circular hose of even wall thickness Ejector vacuum pump—a passive device able to create vacuum, below atmospheric pressure volume, suction to said volume, based on compressed air Membrane—a thin sheet material of non porous character being either flexible or non flexible Pneumatic—pressurized gas, air at higher than atmospheric air pressure CIP—Cleaning In Place SIP—Sterilizing In Place Proportional valves—an analogue output control signal of 0-10 VDC (or digital controlled) from a micro processor to the proportional valve may control the input to allow the valve device to regulate the pneumatic pressure signal within a range from zero pressure to maximum pressure On/off valves—as the name indicates—no variable regulating effect. Just open or closed.

PRIOR ART

Reference is given to U.S. Pat. No. 5,002,471 from D.F. Lab in Israel describing only the pumping membrane, the cell to be disposable. The housing and valves are not disposable also involving mechanical work associated with exchange of the cell or wall. There is no electronics for control and operation of valves disclosed. Vacuum is not mentioned as drive for reciprocating the membrane. The invention will only work if the cell and diaphragm is assembled completely free from entrapped air—not really possible.

Ref is made to U.S. Pat. No. 5,378,122 from company Wilden describing a dual diaphragm pump with its sliding rod/piston connecting the two membranes and for which the pressurized drive air access is controlled by a solenoid valve. With respect to the invention this is an off/on valve and not a proportional valve. The pump characteristics may be changed, as described by altering the piston thickness and it is assumed this is done during manufacturing and not during operation.

Ref is made to US patent 2009-0068032 with the title "Sanitary Diaphragm Pump for Critical Bioprocess Applications" from PendoTECH offer pumping devices that is easily cleaned and/or sterilized after each use hereby not being disposable. A reciprocating piston is in close contact with one side on the flexible diaphragm.

Johan Stenberg from Sweden in US patent 29047137A1 and in WO2007058579A1 describes a control system for an electromagnetic driven diaphragm pump. Though not for a pneumatic operated diaphragm pump.

Van Bork describes in U.S. Pat. No. 5,249,932 the use of membrane position with proximity sensors measuring the distance to the membrane as the membrane is equipped with a permanent magnet. In other words based on electromechanical sensor devices for membrane protection only. The patent does not describe means or methods for position measurements of the membrane along the stroke with the purpose on fluid volume control or proportional regulation of the membrane position.

Novo explains in U.S. Pat. No. 6,948,918 the principle of a small diaphragm pump with free floating membrane in a house. The membrane movement is performed by enclosed fluid on the drive side being heated by external energy, which expands and inflates the membrane.

U.S. Pat. No. 6,544,424 from Refined Technologies describes a diaphragm pump integrated with a filter in a bioreactor set-up. Important characteristics are: There is no disclosure of an arrangement of a displacement sensor, but there is described a proximity sensor being an on/off type of sensor. The device relies on external supply of vacuum. Only 3-way or 4-way solenoid valves are mentioned both being on/off type of valves, and there is no mentioning of the use of proportional valves.

The pharmaceutical industry is looking after single-use diaphragm pumps with a life time of less than 3 month, limited pumping pressure and capacity and super clean media capability. Simple products with housing and membrane from disposable materials for lowering the cost and with the ability of implementation into other devices, like a bioreactor. A combined bioreactor and pump, with both bioreactor and pump bein in single-use configuration, may further eliminate the need for costly CIP requirements.

Despite the many products available around the globe and the comprehensive prior art, no such diaphragm pump is known or available. So please allow the inventor the following presentation.

SHORT PRESENTATION OF THE INVENTION

The present invention provides a diaphragm pump driven by external gas supply with electronic control, such as modern micro-processor control, which may control both membrane and valve actions. The pump may be produced from low-cost materials and may operate from absolute pressure.

In some embodiments of the invention, the pump may be fully disposable and made from polymers. In other versions the part of the pump being in contact with the media or fluid is disposable.

Some embodiments of the invention provide a pump that may be able to operate as a single-use stand-alone unit for the pharmaceutical industry as well as other chemical or biotech industries.

The invention also provide embodiments of a pump, which may be integrated into the same flexible bag, rigid container, or capsule as a bioreactor and/or a purification device, which allows for different methods of use, such as perfusion mode, re-circulation mode, cross-flow mode operation.

According to the invention there is also provided an electronically controlled and operated diaphragm pump able to handle more than one fluid circuit instantaneously.

SUMMARY OF THE INVENTION

According to a first aspect of the present invention, there is provided a diaphragm pump system comprising:
a) a pump housing comprising a drive gas chamber and a fluid chamber separated by a diaphragm; the drive gas chamber being connected to one or more gas ports for injecting and/or sucking a gas into and out of the gas chamber; the fluid chamber being connected to a least one port for fluid inlet and at least one port for fluid outlet, said inlet port(s) having a valve adapted to open for fluid inlet when gas is sucked out of the gas chamber and said outlet port(s) having a valve adapted to open for fluid outlet when gas is injected into the gas chamber;
b) means for providing a drive gas pressure in response to a control signal, said pressure means being connected to at least one gas port;
c) means for providing a gas under-pressure or sucking of gas in response to a control signal, said under-pressure means being connected to at least one gas port;
d) a displacement sensor for detecting displacement or position of the diaphragm;
e) control circuitry connected to the displacement sensor for determining the displacement or position of the diaphragm and adapted for supplying the control signals to the gas pressure means and the gas under-pressure means.

Here, the means for providing the drive gas pressure via a gas port to the gas drive chamber may be adapted for varying the drive gas pressure as a function of the magnitude of the control signal supplied by the control circuitry. The means for providing the gas drive pressure may be adapted for increasing the drive gas pressure with an increase or decrease in the magnitude of the received control signal. It is preferred that the means for providing a drive gas pressure comprises a gas-pressure proportional control valve being connected to the gas port and the control circuitry, whereby the drive gas pressure is varied as a function of the control signal supplied by the control circuitry.

It is preferred that the means for providing the gas under-pressure via a gas port to the gas drive chamber is adapted for varying the gas under-pressure as a function of the magnitude of the control signal supplied by the control circuitry. The means for providing the gas under-pressure may be adapted for increasing the gas under-pressure or increasing the sucking of gas with an increase or decrease in the magnitude of the received control signal. It is preferred that the means for providing a gas under-pressure comprises a gas-under proportional control valve for controlling the gas under-pressure as a function of the control signal supplied by the control circuitry. It is also preferred that the means for providing a gas under-pressure comprises a vacuum pump, such as a vacuum ejector pump, said vacuum pump being connected to a gas port. The vacuum pump may be connected to and driven by the gas under-pressure proportional control valve. The vacuum pump may be connected to the gas port via an on/off valve, the function of said on/off valve being controlled by the control circuitry.

According to an embodiment of the invention the means for providing the gas drive pressure is connected to a drive gas port for injecting gas into the drive gas chamber, and the means for providing the gas under-pressure is connected to an under-pressure gas port for sucking gas out of the drive gas chamber.

The pump housing may be formed of an upper housing part and a lower housing part, wherein the upper housing part holds a fluid chamber wall, which together with the diaphragm forms the fluid chamber, said upper housing part further holding the fluid inlet/outlet port(s) with the fluid inlet/outlet valves. The lower housing part may hold a gas chamber wall, which together with the diaphragm forms the gas chamber, said gas chamber wall holding the one or more gas ports. It is preferred that the upper housing part and/or the walls of the fluid chamber, the fluid inlet/outlet ports and the fluid inlet/outlet valves are made of one or more disposable materials. Here, the disposable materials may be selected from a list including: thermo polymers, thermo setting polymers and elastic polymers. It is also preferred that the diaphragm is made of a disposable material, which may be selected from a list including: synthetic or natural elastic polymers.

For embodiments having a lower housing part, the displacement sensor may be arranged in the lower housing part and outside the gas chamber, and here the displacement sensor may be arranged in the lower housing part below the gas chamber wall.

It should be understood that the present invention covers embodiments with different types of displacement sensors based on different operation principles such as for example: capacitive sensors, eddy current sensor, inductive sensors, laser sensors, optical sensors, confocal sensors, digital camera type sensors. It is preferred that the displacement sensor is an optical type displacement sensor. It is also preferred that the displacement sensor is a laser type displacement sensor. The displacement sensor may be arranged below a transparent window provided in the gas chamber wall, to thereby permit optical sensing of the diaphragm displacement/position.

For embodiments having a lower housing part, the proportional valves and the vacuum pump may be arranged in the lower housing part and outside the gas chamber. The control circuitry may also be arranged in the lower housing part below the gas chamber wall.

The first aspect of the invention also covers embodiments, wherein the pump system further comprises a pressure sensor for detecting fluid pressure within the fluid chamber, said fluid pressure sensor delivering a fluid pressure signal to the control circuitry. A pressure sensor window may be provided in the fluid chamber wall with a fluid pressure sensor provided at said fluid pressure sensor window. The pressure sensor window may be flexible and may also be integrated with the pressure sensor. The system of the first aspect of the invention may also comprise a temperature sensor for detecting the temperature of the fluid within the fluid chamber and for delivering a fluid temperature signal to the control circuitry. According to an embodiment of the invention a single sensor unit may comprise the fluid pressure sensor and the fluid temperature sensor.

The system of the first aspect of the invention may also comprise a pressure sensor for detecting gas pressure within the drive gas chamber, said gas pressure sensor delivering a gas pressure signal to the control circuitry. Here, a gas pressure sensor window may be provided in the gas chamber wall with a gas pressure sensor provided at said gas pressure sensor window. Here, the gas pressure sensor window may be flexible and may also be integrated with the pressure sensor A number of different types of fluid valves may be used in the pump system of invention, and the fluid inlet valve and the fluid outlet valve may be selected from a list of valves including: passive check valves, electro mechanical controlled valves, guillotine/pinch valves, sleeve hose valves, diaphragm valves, and pumping diaphragm sequential valves.

According to one or more embodiments of the first aspect of the invention, each of the fluid valves may function both as an inlet valve and as an outlet valve, where the function of the valves is controlled by the control circuitry. In a preferred embodiment the fluid valves are sleeve hose valves.

For driving of the gas chamber, the system of the first aspect of the invention may further comprise a connection for external supply of pressurized drive gas. The connection for external supply of pressurized drive gas may further be connected to the means for providing a drive gas pressure and the means for providing a gas under-pressure. The connection for external supply of pressurized drive gas may be connected to the gas pressure proportional valve and the gas under-pressure proportional valve. Preferably, the connection for external supply of pressurized gas is arranged at the lower housing part of the pump housing.

According to an embodiment of the first aspect of the invention, the upper housing part and the parts being hold by the upper housing part are made of disposable materials, which may be selected from a list including: thermo polymers, thermo setting polymers and elastic polymers. It is also within embodiments of the first aspect of the invention that the lower housing part is made to be re-usable.

According to a second aspect of the invention there is provided a pump system comprising two or more diaphragm pumps, where the diaphragm pumps are selected from any of the embodiments of the pump system of the first aspect of the invention, and where the pumps are coupled in parallel so that the fluid inlet ports are coupled in parallel and the fluid outlet ports are coupled in parallel. It is preferred that the drive gas pressure of the pumps coupled in parallel is controlled to be out of phase as a function of time. According to an embodiment of the second aspect of the invention, the system has two pumps coupled in parallel, and the drive gas pressure of the two pumps is controlled so as to have a phase displacement of about 180 degrees. According to another embodiment of the second aspect of the invention, the system has a first, a second, a third and a fourth pump being coupled in parallel, and the drive gas pressure of the four pumps is controlled so as to have a phase displacement of about 90 degrees from the first to the second pump, from the second to the third pump, and from the third to the fourth pump, respectively.

According to a third aspect of the invention there is provided a pump system comprising two diaphragm pumps, where the diaphragm pumps are selected from any of the embodiments of the pump system of the first aspect of the invention, and where each pump has a first, a second, a third and a fourth fluid inlet/outlet port, each fluid inlet/outlet port having a corresponding fluid inlet/outlet valve, said fluid inlets/outlet ports being connected in pairs with the two first inlet/outlet ports connected to a first common inlet/outlet port, the two second inlet/outlet ports connected to a second inlet/outlet port, the two third inlet/outlet ports connected to the a third common inlet/outlet port, and the two fourth inlet/outlet ports connected to a fourth common inlet/outlet port. It is preferred that each of the fluid valves can function both as an inlet valve and as an outlet valve, the function of the valves being controlled by the control circuitry of the corresponding diaphragm pump. In a preferred embodiment the fluid valves are sleeve hose valves.

According to a fourth aspect of the invention there is provided a bioreactor system comprising a first and a second diaphragm pump system and a bioreactor having one or more bioreactor modules, wherein:
  at least one bioreactor module has an inner collection volume, a porous matrix at least partly surrounding the inner collection volume, and an outer collection volume at least partly surrounding the porous matrix;
  the first pump system has a fluid inlet port with a fluid inlet valve for external inlet of fluid to a fluid chamber, a first fluid outlet port having a fluid outlet valve and being connected to the bottom of the inner collection volume of the bioreactor for outlet of fluid from the fluid chamber to the inner collection volume, and a second fluid outlet port having a fluid outlet valve and being connected to the bottom of the outer collection volume of the bioreactor for outlet of fluid from the bioreactor; and
the second pump system has one or more fluid inlet ports being connected to the top of the outer collection volume of the bioreactor, each said inlet ports having a fluid inlet valve and further being connected to a fluid chamber of the second pump system for inlet of fluid from the outer collection volume to the fluid chamber, and a fluid outlet port having a fluid outlet valve and being connected to the top of the inner collection volume for outlet of fluid from the fluid chamber of the second pump system to the inner collection volume. Here, the first pump system may correspond to a pump system selected from any of the embodiments of the pump system of the first aspect of the invention, and further comprise the second fluid outlet port connected to the bottom of the outer collection volume. Also the second pump system may corresponds to a pump system selected from any of the embodiments of the pump system of the first aspect of the invention.

According to an embodiment of the fourth aspect of the invention, the bioreactor may comprise two, three or more bioreactor modules having an inner collection volume, a porous matrix at least partly surrounding the inner collection volume, and an outer collection volume at least partly surrounding the porous matrix, and wherein said bioreactor modules are stacked on top of each other.

According to an embodiment of the fourth aspect of the invention, the first pump system may correspond to a pump system selected from any of the pump systems of the first aspect of the invention having an upper housing part and a lower housing part, and with the second fluid outlet port being arranged in the upper housing part. Also the second pump system may correspond to a pump system selected from any of the pump systems of the first aspect of the invention having an upper housing part and a lower housing part. The upper housing part of the first pump system may be facing the bottom of the bioreactor and the upper housing part of the second pump system may be facing the top of the bioreactor. The upper housing parts and the parts being hold by the upper housing parts of the first and second pump system may be made of disposable materials. Also the bioreactor modules may be made of disposable materials. Such disposable materials may be selected from a list including: thermo polymers, thermo setting polymers and elastic polymers.

According to a fifth aspect of the invention there is provided a sleeve valve assembly comprising:
  a first valve housing having first and second fluid inlet/outlet ports and a first gas inlet port;
  a first core arranged centrally within the housing; and
  a first elastic tube sleeve in gas tight connection with the inner side wall of the first housing and connected to the first gas inlet port, said first elastic tube further surrounding the first core, whereby an inflation of the first elastic tube sleeve by pressurized gas through the first gas inlet port expands the first tube sleeve inwards to collapse around the first core, thereby closing for fluid flow through the first valve housing. Here, the inner side wall of the first valve housing may be of a substantial rotational symmetrical design with the first and second fluid inlet/outlet ports being oppositely arranged, and the first gas inlet port may be arranged in the wall between the fluid inlet/outlet ports. The first core may be a rotational symmetrical core attached at a first end to a perforated wall, said perforated wall being arranged at a first end of the first valve housing and connected to the first fluid inlet/outlet port.

The fifth aspect of the invention also covers an embodiment wherein the outer side wall of the first valve housing is of a substantial rotational symmetrical design, and wherein the sleeve valve assembly further comprises:
  a second core surrounding the outer wall of the first valve housing;
  a second valve housing surrounding the second core and having first and second fluid inlet/outlet ports and a second gas inlet port; and
  a second elastic tube sleeve in gas-tight connection with the inner side of the second valve housing and connected to the second gas inlet port, said second elastic tube further surrounding the second core, whereby an inflation of the second elastic tube sleeve by pressurized gas through the second gas inlet port expands the second tube sleeve inwards to collapse around the second core, thereby closing for fluid flow through the second valve housing. Here, the inner side wall of the second valve housing may be of a substantial rotational symmetrical design with the first and second fluid inlet/outlet ports being oppositely arranged, and with the second gas inlet port arranged in the wall between the fluid inlet/outlet ports. The second core may be a rotational symmetrical core being gas-tight connected to the outer wall of the first valve housing.

For the sleeve valve assembly of the fifth aspect of the invention it is preferred that the first tube sleeve has a triangular form, and that the first core has a groove or notches for receiving the top of the first tube sleeve when inflated. It is also preferred that the second tube sleeve has a triangular form, and that the second core has a groove or notches for receiving the top of the second tube sleeve when inflated.

According to a preferred embodiment of the fifth aspect of the invention, all the parts of the sleeve valve assembly are made of a disposable material. The disposable materials may be selected from a list including: thermo polymers, thermo setting polymers and elastic polymers.

BRIEF DESCRIPTION OF THE DRAWINGS

FIG. 9 shows a perspective look of a second embodiment of a sleeve valve assembly according to the invention, FIG. 10 is a cut view of the sleeve valve of FIG. 9.

DETAILED PRESENTATION

Figure 1:
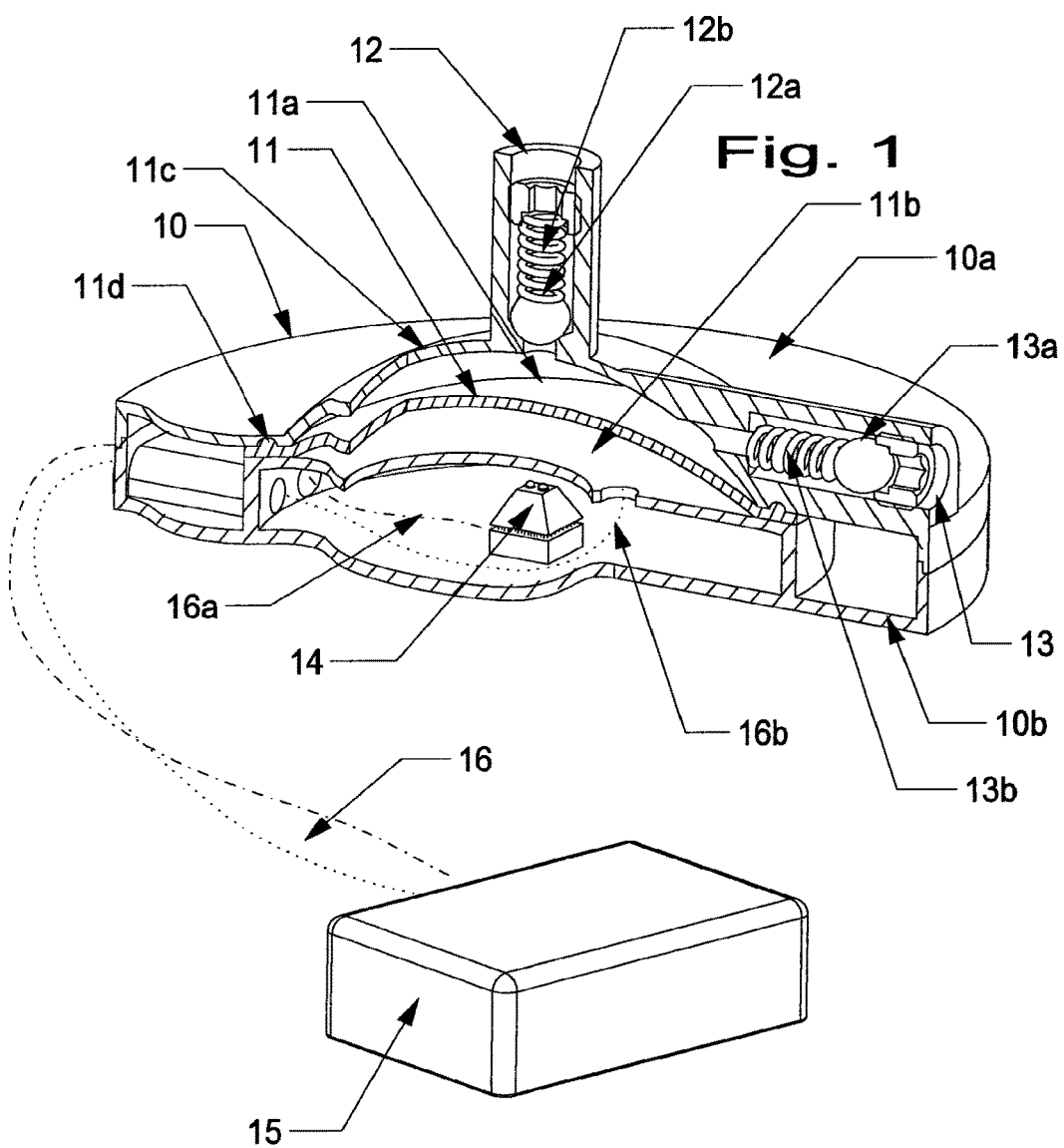
FIG. 1 shows a first embodiment of a diaphragm pump system according to the invention, where the system comprises a single diaphragm pump.

The invention provides embodiments of diaphragm pumps, which may be manufactured preferably from plastics and elastomeric materials. The diaphragm may be controlled, driven respectively, by over-pressure and under-pressure on one side of the diaphragm only. External supply of pressurized air may supply both the over-pressure and through an integrated vacuum injector pumps also the under-pressure. The pump circumference may be an assembly in which the flexible diaphragm membrane is gas and liquid tight secured. The pump may be based on at least one single membrane creating the pump device. One end face of a short cylindrical housing may be covered gas and liquid tight with a disc of elastic material creating two volumes/rooms, one on each side of the membrane. One room may face the fluid to be pumped to define a fluid chamber, and the opposite room may provide a gas chamber for motion control of the membrane by gas pressure. The membranes may take other shapes than round. Spring loaded ball valves, though preferably fully electronically controlled valves, may control the fluid path through the pump. An important part of the invention may be an integrated electrical control device, which based on input from various sensors may be fully responsible for the pumps functions. Benefits of the invention may be low pricing, truly single-use capability, high capacity with low fluid speeds, low fluid shear forces, low damaging of the potentially circulating particles/cells when combined with a bioreactor.

The pump may be integrated into various devices, potentially with the same house diameter and pump height adjusted according to capacity. Such as combined with the CerCore bioreactor concept described in patent application DK/PA/2008/001815 and DK/PA/2009/01165, which describes a three-dimensional porous matrix based bioreactor, which may eliminate the gradient problem seen in all bioreactors seeded with micro organisms. Two separate pumps may be used facing towards the bioreactor, one from each end. In the control part of the pump, a gas supply connection may offer external connection to a supply of gas pressure and/or combined gas pressure above and below atmospheric pressure, thereby serving as the force for operating the pump. The control part of the pump may all be outside the bioreactor environment with fewer demands to sterile conditions. Pump integration is further described in patent application CerStack patent application DK/PA/1009/001142.

Pump Variations

A single membrane pump according to the invention is based on a flexible diaphragm element with the fluid to be pumped on one side only, and a separate fluid, preferably gas for drive purposes on the other side of the membrane. The movable wall between the two chambers allows sterilization on one side and full separation of drive gas and pumped fluid on the other side.

1. The pump is based on a single diaphragm set-up, which it is possible to integrate in various configurations.
2. Two single diaphragm pumps of identical diameter may work in parallel facing each other for increased volumetric capacity and different pump characteristics. Such as when two diaphragm membranes are working towards each other, in parallel, only separated by a fluid chamber. Or two pumps may be positioned with the drive gas chambers towards each other, like the more traditional diaphragm pump set-up, for low pulsation effects, but without the traditional rigid coupling to the membranes. In such an application the two pump parts may correspond both via electronic signals as well via sharing the same fluid inlet and outlet.
3. Two single diaphragm pumps of different diameter membrane may work in series for increased pumping pressure in a step-up hydraulic motion. The larger membrane with the gas drive on one side has a fluid contact on the other side with a constant volume. The smaller membrane is in contact with the fluid on its drive side and on the other side in contact with the media to be pumped. The larger membrane forces the smaller membrane to amplify the pressure. The second and smaller membrane working media pressure and stroke is amplified proportional to the difference in membrane diameter to the larger membrane.
4. When a single diaphragm pump of the invention is integrated with a bioreactor (or other device), the nutrient velocity dynamics and flow profile though the matrix may have huge impact on the spontaneous deposits of the micro organisms prior to colonization. Relative strength of cell adhesion to the support is related to initial surface tension of the matrix surface and reflects the integrity of the first conditioning films, which is usually dominated by proteins. Fluid flow effects, such as shear stresses, play a critical role in the process during cell seeding. A pump with unlimited control features will promote such benefits during seeding.

The diaphragm pump of the invention may have a flow capacity ranging from ml/sec to m3/hour depending of diaphragm diameter and stroke. The smallest pumps may have a 30 mm diameter diaphragm. As an example, then for at 3 l bio reactor, the pump capacity may be between 10-20 l/hour depending on operating principle, which is possible with a diaphragm diameter of 100 mm. In the upper capacity end, a 0.5 m diameter single membrane will have a capacity in the range of 40-50 m3/hour.

Diaphragm Membrane Design

The reciprocating flexible piston is preferably an elastomeric membrane diaphragm based on amorphous polymers cut from sheets or shaped, like during casting into shape, or more advanced shapes like in a corrugated shape with bellows in the circumference. The membrane could alternatively be manufactured from thin foil shaped into corrugated structure with the ability to flex in axial directions.

The pumping diaphragm membrane may have in its centre wires or particles included, attached to the surface for improved recognition and accuracy in sensing by a displacement sensor, such as by reflection of magnetic forces, capacitive measures, radio frequency waves, light reflection, etc. With print on the membrane a camera may be able to pick up the distance between figures as measures of expansion of the membrane. Furthermore, a laser-based device may accurately inform the control circuitry or micro-processor about the actual distance and speed of motion online.

The diaphragm membrane is further preferably manufactured with asymmetric properties. Such as variations in thickness from the circumference radial to the centre of the membrane. And/or be laminated from materials with different properties in selected areas. The membrane may further implement re-enforcements like wires and/or threads to avoid elongation of the elastomer in selected areas, such as in the circumference, where the membrane is in contact with the housing parts.

In accordance with the present invention the membrane may further employ a series of radial oriented ribs extending at least partially from the centre to the outer perimeter. The ribs may be integrated with the membrane on one side only or on both sides only and if desired in combination with a centre located ring of the same or different high as to the ribs.

The membrane may further facilitate a support for a spring on at least one side of the membrane in order to alter the functionality of the pump according to the primary intention of the invention. During operation of the pump, by adding drive gas under pressure into the drive chamber, the spring will be compressed as well as the fluid is forced out through the exhaust valve and channels. The compressed spring will force the membrane to return to its deflated position and applying a suction effect in the pump when inflation drive gas is released.

Valve Variations

Fluid conveying valves may by rigid elements or flexible elements, and may take multiple shapes such as: floating discs, fixed elliptic discs, mushroom valves, ball valves, hoses, etc. The fluid valves may be of non-controlled, controlled character and based on disposable materials. The valves described and connected to the pumping device may be inlet or outlet valves.

1. Check valves or one-way valves are the normally passive, non-controlled ball design with action controlled by simple helical springs or just gravity controlled. Check valves are closed in one direction and open in the opposite direction. The conveyed fluid lifts the ball from its seat by overcoming the gravity effect or spring force allowing the fluid to pass. For alternative application the check valve may not be a ball, but a diaphragm or disc made from materials with desired properties. The diaphragm may be single sheet or laminated from rigid and flexible materials covering a valve seat. Operation may be assisted by a spring, but in general fully controlled by the material stiffness. Flap valves are typically metal sheet pieces, but may be plastic strips, discs with desired flexibility to insure motion and spring back effects. Metallic blades in the valve with electro magnetic control may support oscillation for variable mass flow.

2. Electro mechanical controlled valves may be a ball with a circular magnetic core covered with plastics operating in a reciprocating motion inside a valve body with an inlet/outlet integrating a round electro magnet in the valve body being a coil with a centre hole around the fluid channel and ball seat/seal. The motion distance is short, like few millimeters to ten millimeters, precisely controlled for ball to be attracted or distracted to the valve seat. In such an arrangement the valve do not need a spring for closing, but only two wires to the control device for adding the DC voltage with positive voltage in one or the other direction according to desired ball position—open or closed. Mushroom valves operate reciprocating in guides with a valve head against a seat controlled by springs and/or magnetically forces. Low specific weight metallic core balls in the valve with electro magnetic control may support oscillation for variable mass flow.

3. Guillotine/pinch valves function by axial action of a flat plate being a part of a circular piston oriented perpendicular to the flexible hose secured in a groove. Adding forces to the flexible hose allow collapsing to occur and the cross section is reduced to zero, which closes for the fluid transfer. The pistons reciprocating motion controlled by pressurized air (alternatively a solenoid armature) in the closing action and pressure less the piston return to the valve open position of the hose and/or a spring. The guillotine valve benefits from low pressure drop, being easily manufactured from disposable materials, its simple control characteristics and its low prize.

4. Sleeve hose valves are designed to collapse around a sealing body as gas pressure is supplied to the opposite side of the media contact side of the sleeve hose. The sleeve valve may take the inner or outer approach as the closing contact body may be outside of the sleeve hose or inside of the sleeve hose. In either way the sleeve valve benefit from contact with a circular surface with at least one groove. In case of the sleeve hose valve with gas pressure on the outside, then the inner side of the sleeve hose collapse preferably onto the surface of a central core. Typical operation as on/off valve, but by controlling the pressure the valve may change cross section and become a proportional valve. The sleeve hose valve design benefits from low pressure drop, being easily manufactured from disposable materials, its simple control characteristics, gentle operation, extreme lifetime, tolerance to particle containing media, operation by pneumatics and its low prize.

5. Diaphragm valves are flexible sheets of limited size operating with gas pressure on one side against a circular seat though which the media/fluid passes unhindered when no drive gas pressure is added to the flexible sheets opposite side. The sheet of flexible material may be gas and liquid tight integrated at its complete circumference between two housing parts during assembling. One housing part facilitating integrated channels to convey the fluid, the other housing part with one relative small diameter channel to supply the pressurized air to the drive side of the flexible membrane. Distance from the diaphragm to the seat determines functionality such as being a normally open or normally closed valve.

6. Pumping diaphragm sequential valve function is an option even it the primary action is as a piston for pumping. The diaphragm may facilitate closing or opening of a valve in its centre benefited by the sharply controlled diaphragm motion. Such a valve may be a typical one-way spring loaded ball valve equipped with an extra rod passing through the valve body exposed into the membrane fluid chamber. When the diaphragm selectively is inflated to the last few percent the valve rod is reached and the valve opens.

Housing Variation in General

The pump house is preferably pressure cast from rigid materials such as plastics in order to be easily disposable. The house parts may employ ribs for re-enforcement, which may further act as fluid guides simultaneously. Porous parts may be introduced in order to control drainage or fluid control. The house may include volumes of cylindrical shape to convey fluids and give rooms for introduction of valve modules. The housing or part of the housing may further hold or include a vacuum storage volume for a reduced responsiveness for the diaphragm. The vacuum storage volume may also be for a reduced responsiveness for the valves.

Operational Features in General

The pump can control the fluid flow by an analogue and/or a digital signal and identify the present vacuum or pressure for regulation. On-line controlled variables are such as: maintain a constant flow independent of the load, continuous pressure independent of flow, create or avoid pressure oscillation, pump a fixed volume, specified number of strokes, different stroke length, constant pressure, synchronize with other measures, etc. The characteristics of the pump is limited only by the programmer's imagination—compared to prior art diaphragm pumps operating purely mechanically without any programming capability.

Operational Features Combined with a Bioreactor

With the integration of the pump of the present invention with the CerCore bioreactor the resulting device may become the leading edge 100% single-use, high productivity concept. Heating or cooling devices may be integrated in the top housing of the pump with direct contact to the media being pumped to the bioreactor. Heating alternatively performed via integrated channel conduits, which convey liquid from an external liquid supply at desired temperature. Preferably, temperature conditioning is performed by electric resistance elements with fluid exposed to the heaters cast into the housing walls/surfaces. The electrical elements may be connected to a power supply in a pump control module to supply sufficient heat according to losses for constant temperature. The pump of the invention, which may be a single-use pump, may serve several periodical tasks, such as:

Re-circulation for perfusion mode operation
Correspond with the fresh media storage
Correspond with the product/used media storage easily controlled by the control device assisted by a suitable amount of solenoid build-in valves into the various fluid circuits.

Each manufacturer of fermenters/bioreactors supply their own specialised control systems working only in this specific set-up. The present invention may eliminate the need for being loyal to only one supplier, as the overall control now may be performed by a PC.

More than one of the invented pump devices with similar or different capacity may be included into one bioreactor set-up.

A combination of a pump of the invention and a control device of the invention further allows the important features of control of more than just one pumping circuit—within the same pump. More than one set of valves allows several circuits connected to one pump. When the primary set of several inlet/outlet fluid valves are solenoid controlled their operating is fully controllable in time and performance. When the primary valves are closed other sets of secondary solenoid controlled valves may open for a secondary fluid circuit with external fluid containing containers or devices. Such as, allowing the bioreactor/fermenter to correspond sequentially with an upstream fresh media supply or sequentially with a down stream processing device, all within the same Biopharmaceutical Processes Plant set-up. The new features may eliminate the typical dependency of several peristaltic pumps, reduce the number of hoses, connectors in such a set-up, all in all with benefits of being sterile and at lower cost.

Diaphragm Drive Source

The presented diaphragm pump performs with both vacuum and pressurized air to move the diaphragm between its end points while pumping the media. For simplified operation the pump may only need traditional air supply like 4-6 Bar pressure. The diaphragm motion may be controlled on the drive gas chamber side by the carefully controlled driving gas pressure variables around atmospheric pressure. Higher than atmospheric is the prime driver for the diaphragm stroke moving fluids. Lower than atmospheric pressure needed to return the diaphragm to starting position, when fluid is supplied to the pump chamber. If passive one-way valves is used this low pressure also operates the passive one-way valves and overcome possible valve spring effect and fluid friction. If only pressurized air is available, the control device may be somewhat different, as it must include a pressurized air/vacuum converter combined with a driving proportional valve. Compressed air driven vacuum pump technologies are well known in the industry and supplied also by the Swedish company Piab AB or US based Parker or German Festo. Single or multi stage ejector pumps like the Coax with no moving parts, small and easy to implement and are able to generate at least minus 75 kPa atmospheric pressure or better than 25 kPa absolute pressure.

When gas pressure is measured from absolute pressure, we take the universe pressure as the starting point. On the other hand, we on globe earth live at 1 bar absolute pressure. Though we often refer global surface pressure as being zero bar, Pascal, etc. So the pump of the present invention may be able to operate at pressures ranging from absolute zero to pressures above global pressure. Or the pump is able to operate, seen from global perspective, with vacuum and pressure.

Pump General Control

The pumps control device may operate based on the action signal to constantly adjust the fluid valves and the membrane to any position between 0-100% stroke based on:
  DC power supply such as 12 or 24 VDC for powering valves, sensors, micro processor.
  Action signals from a PC/PLC to the micro processor.

The pumps control device may preferably take advantage of an embedded micro processor, and may receive various input measurement signals, like:
  Diaphragm positions sensor signals, such as based on: capacitive, eddy current, inductive, laser, optical, confocal, digital camera types;
  main/external gas pressure supply;
  diaphragm pump drive gas chamber pressure between absolute and plus 5 bar;
  diaphragm pump fluid chamber pressure;
  gas discharge pressure;

temperature sensor in pump;
temperature sensor in bioreactor;
extra flow sensors;
integrated disposable sensors for pH, oxygen, carbon dioxide, temperature, etc;

The control device circuit board may hold at least one micro processor with an associated program and working memory for storing algorithms, programming, and various power supplies, regulating power output channels in order to control among others:

Proportional gas pressure inlet valve connected to the diaphragm gas chamber;
Proportional gas pressure exhaust valve;
Proportional fluid valve control if desired via solenoids or integrated wire coils;
Proportional power control for temperature conditioning purposes in the pump;
Proportional power control for temperature conditioning purposes in the bioreactor;

Specifically with digital control, the fluid line valves performance may easily be controlled since rather unlimited information may be transferred. The performance of the inlet/outlet valves may via electro-magnets/solenoids be controlled for such operation as opening, closing, ramp, and duration.

Empty traditional diaphragm pumps being started (with no load) may typically have huge difficulties in stabilizing, which may cause internal damage to the pump. This phenomenon may fully be eliminated with the herein presented pump and its control. The control device of the invention does not need to be disposed after use, but may preferably be re-used. The built in micro controller may on pump house replacement look for internal stored algorithm in its memory and adjust the new attached pump conditions hereby handling pump production tolerances. Similarly, the heating jacket on the bench-top bioreactor may be re-used.

The invented pump may be a positive displacement pump with internal very accurate control of the actual pumped volume. As to the membrane displacement sensor the control device may be able to give information about volume pumped online, over time and to pump a specific volume and inform such data to the PLC.

Additional Sensors

According to embodiments of the invention, the pump may further be connected in series with flow sensors, which may be disposable flow sensors, and which signal may give further input to the control circuitry or micro processor of the control device for even more strict volume control. Disposable flow sensors are available from vendors like Clarck Solutions Inc in the US and SciLog Inc. with standard flanges in ¾" and 1" size for max 60 liter/min flow. Correspondence via RS-232/RS-485 signal type or analogue 4-20 mA signal. Other brands are PendoTech also from US being disposable in smaller sizes and the German Gemü, who also offer ultrasonic sensors.

Pump Communication

A typical diaphragm pump has no electrical signal communication—it only has the air supply, and the pump only operates when pressurized air is connected.

Compared to analogue operation, a digital signal bus is preferred as to its unlimited capabilities. Several industrial standards (such as Profibus, Fieldbus, Canbus, Modbus, etc) are able to control the pump through Ethernet, wireless network, RF, power-line-communication connection and various valve actions. Operation control such as of opening, closing, ramps, duration, both of the membrane and the valves may further reduce the natural pulsation effects of the invented pump. A built-in pressure sensor in the bottom housing chamber may sense the pressure on-line at certain collection speed and the signal may allow the micro controller to control the proportional valves.

Proportional valves may be beneficial, such as for: one for the supply gas to the diaphragm, one for the diaphragm exhaust gas, and one for the vacuum injector pump. All proportional valves may be controlled by the control circuitry or the micro processor of the control circuitry.

Software Consideration

The control circuitry with micro processor and its associated memory allows for programming and memory storage of several standard pump routines, taken into consideration, such as:

Start-up empty—max frequency before pressure readings—ramp steepness to full pumping capacity.
Primary circuit—secondary valves closed—membrane hold—time.
Primary inlet valve opening—wait for pressure readings in drive gas chamber.
Primary discharge valve opening—wait for pressure readings in fluid chamber.
Capacity—active control dependent—length of stroke and frequency.
Secondary circuit—primary valves closed—membrane hold—time.
Primary inlet valve closed—wait for pressure readings in drive gas chamber.
Primary discharge valve closed—wait for pressure readings in fluid chamber.
Stationary function at selection position.
Inlet pressure supplied—pressure reading—alarm for low drive pressure.
Leak test function.
End of function—pump body replacement.

The external action signals determine:
Pump start and stop.
Pump capacity.
Pump ramping.
Fluid circuit selection.
Optional heating supply.

All features completely un-heard of with traditional diaphragm pumps. Several real-time control loops in the micro processes may insure the desired operation.

The regulating functions may be based on non-linear, adaptive, fussy logic, slide mode control, PI(D) regulation and combinations hereof. The sequence of events or regulation loops preferably in a hieratic set-up with internal loops and external loops with individual data sampling speed being in the range of 0.1 to above 10 kHz. At start up of the pump, the control device preferably performs a diagnostics routine with events based on protocols stored in flash.

At any time, regulating algorithms may use sensor signals for comparison with the action signals to adjust the actual membrane position. If designed to operate by analogue input signals, pulsating of the input signal with ramp steepness, duration and ramping down may control the pump volume. If the input signals from the PLC demand a certain time from position 0% to reach position like 63% of the membrane maximum stroke, the control device may insure a ramp to 63% membrane position regardless of fluid system pressure. And vice versa to return to the starting position of the membrane.

Detailed description of preferred embodiments of the invention

FIG. 1 shows a first embodiment of a stand-alone reciprocating membrane pump 10, which may comprise single-use materials, and which has a single diaphragm 11, operating actions being by pneumatics, which may be from absolute pressure to over atmospheric pressure, the pump being micro processor controlled with various sensors and principles, and in its most simple form with two spring loaded plunger body check valves 12a, 13a in the fluid stream.

The flexible diaphragm 11 may be of circular shape and enclosed at the circumference in order to seal each side of the diaphragm from access to the other diaphragm side within the housing. The diaphragm 11 circumference shape is compatible with the recess 11d in the housing parts 10a, 10b. One side of the diaphragm 11 is exclusively in contact with the fluid 11a to be pumped, and the other side exclusively in contact with the drive gas 11b. At least one side of the diaphragm house 11c is of concave design.

The fluid/media side 11a of the diaphragm 11 is in contact with both fluid outlet 12 and fluid inlet 13 and both the inlet and outlet are equipped with one-way, check valves 12a, 13a operating in opposite direction. The example shown if FIG. 1 illustrates check valves 12a, 13a with circular spring 12b, 13b loaded circular body with fluid conveying holes facing towards the valve seat. Fluid path is through the inlet passage 13 and the inlet check valve 13a, which opens when the diaphragm 11 moves from its expanded, inflated position to the opposite, relaxed position by drive gas exhaust combined with vacuum sucking the diaphragm 11 towards the conical wall 11c of the chamber containing the drive gas. When the diaphragm 11 moves from its relaxed position by inflation with drive gas the fluid is conveyed passing the now open outlet valve 12, but not through the inlet 13 with the check valve 13a now locked towards the seat.

Absolute gas pressure may return the membrane 11 to its relaxed position by vacuum obtained from a built in vacuum injector pump driven by a supplied pressurized gas/air, which also inflates the diaphragm. The actuator/gas side 11b of the housing may be equipped with support for diaphragm displacement sensor(s) 14.

All other instrumentation/actuators may be mounted inside control unit box 15, such as: pressure sensor(s), proportional valve(s), micro processor, and include connections to driving gas inlet/outlet. Gas pressure on the drive side of the diaphragm is regulated by proportional valves controlled by the micro processor. An absolute pressure sensor measures on-line the actual gas pressure in the drive gas chamber. The position of the diaphragm 11 is measured by a displacement sensor 14 and the information used by the micro processor, being part of the control circuitry, to adjust/correct the diaphragm position on-line. The box 15 is via the set of cable and hose 16 connected to the pump module 10 with the cable 16a connected to the displacements sensor and the hose 16b connected to the drive chamber 11b.

Figure 2:
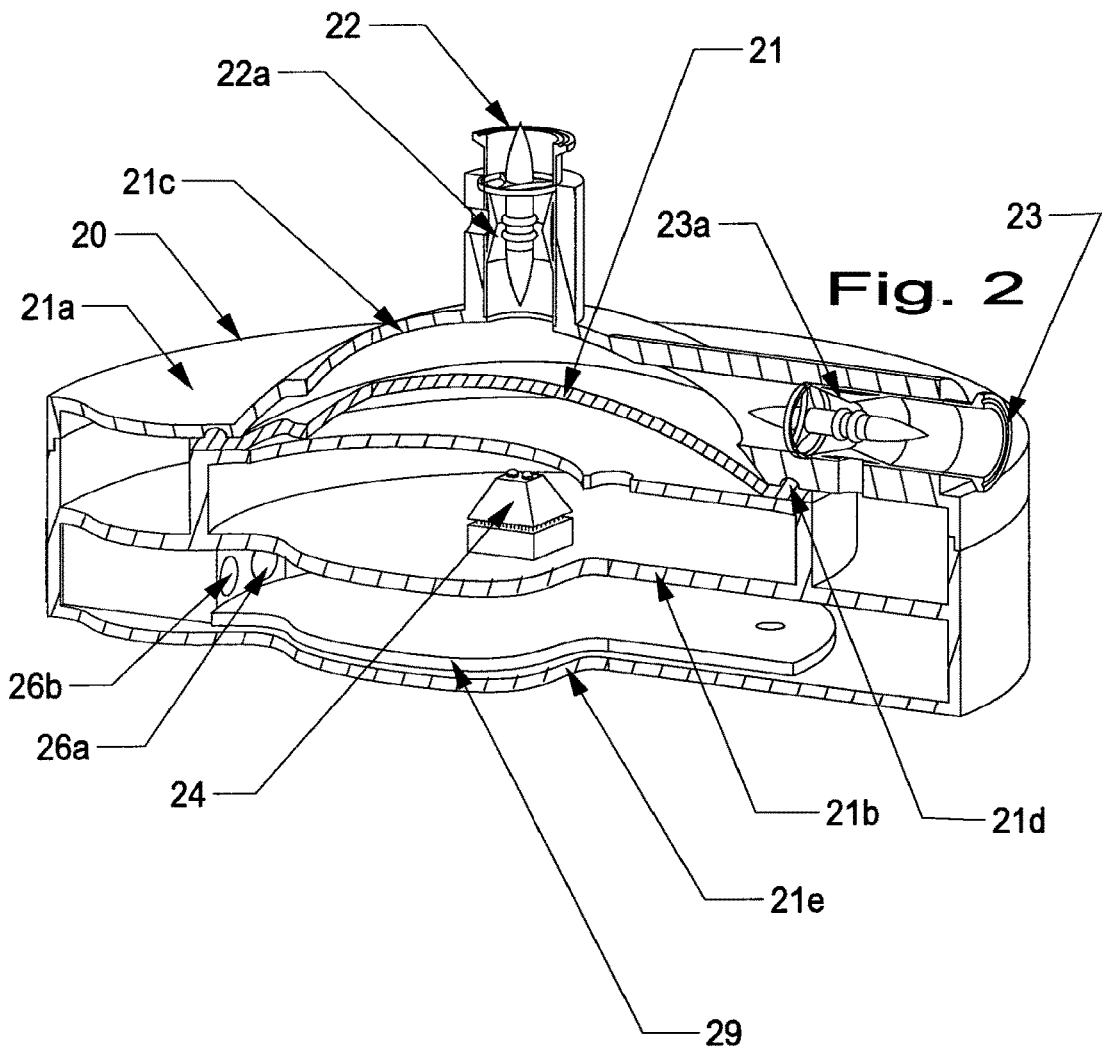
FIG. 2 shows a second embodiment of a diaphragm pump system according to the invention, where the system comprises a single diaphragm pump.

FIG. 2 shows a second embodiment of a stand-alone reciprocating membrane pump 20, which may comprise single-use materials, a which has single diaphragm 21, the operating actions being by pneumatics, which may be from absolute pressure to over atmospheric pressure, the pump being micro processor controlled with various sensors and principles, and in its most simple form with two expansible tube valves 22a, 23a in the fluid stream.

The pump of FIG. 2 has two rigid housing parts 21b, 21c on each side of the flexible diaphragm 21, and assembled on the circumference. The pump 20 also includes a PCB 29 (no electronic parts shown) arranged at the bottom house part 21e. The diaphragm membrane 21 comprises a cast on half O-ring on the diaphragm circumference, which act as the sealing element in the recess 21d on housing part 21a. Diaphragm control is in principle similar to the pump of FIG. 1, the difference being the introduction of expansible tube valves 22a, 23a for extended control of fluid flow. The media/fluid valves 22a, 23a with tri-clamps 22, 23 are elastic tube sleeve based valves located tight in house 21 and identical to the valves further described in connection with FIGS. 7 and 8. When inflated by pneumatics added to the outside of a tube sleeve, the tube sleeve collapses around a central core/torpedo part thereby eliminating media/fluid flow. The valve accepts flow in each direction and behaves gently to media with particles such as alive micro organisms. The pumps 22a, 23a may have inlet or outlet at any port 22, 23 as desired. Two ports 26a, 26b may facilitate connection of electrical and pneumatic power.

Figure 3:
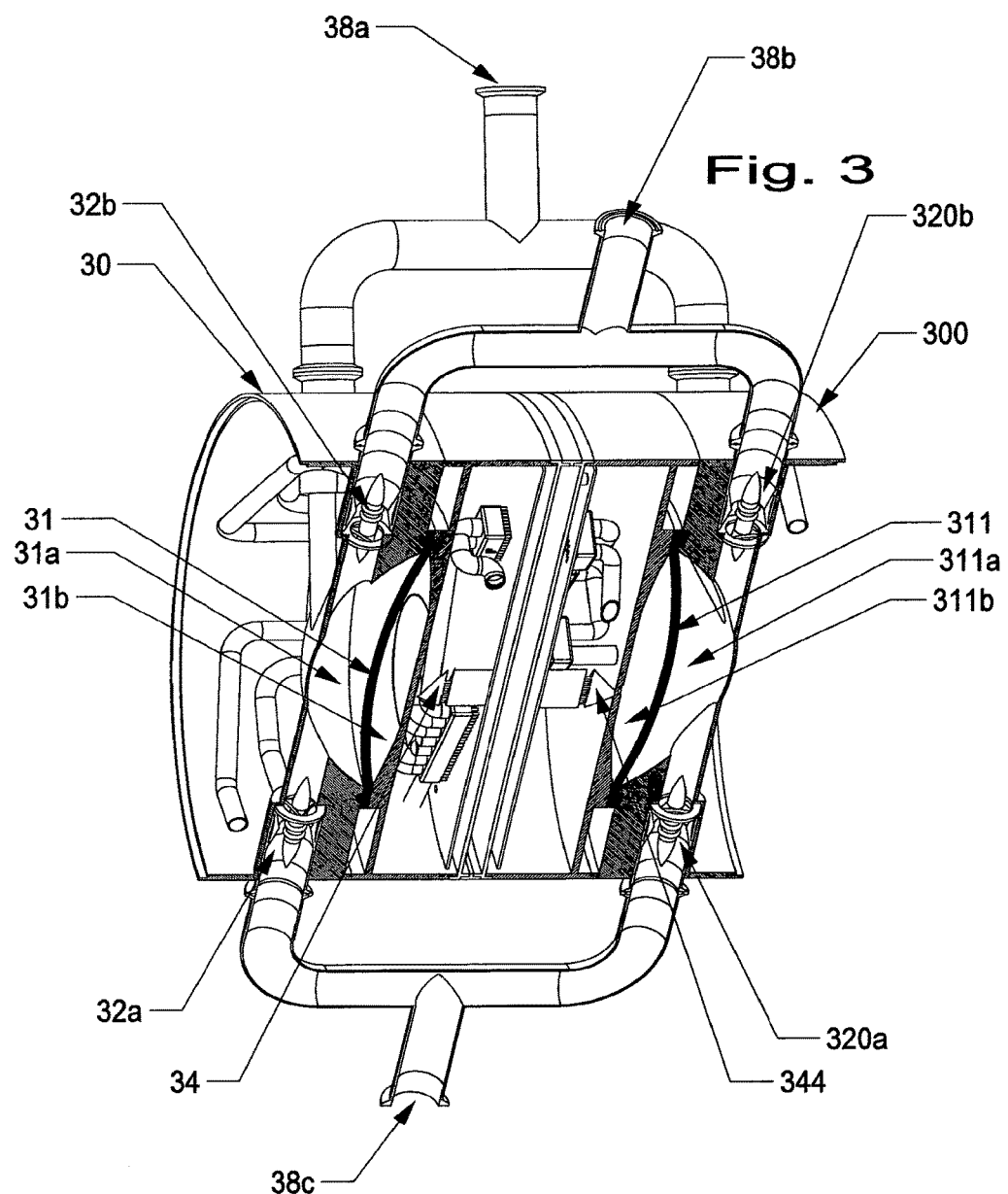
FIG. 3 shows a third embodiment of a diaphragm pump system according to the invention, where the system comprises two diaphragm pumps.

FIG. 3 shows a third embodiment of a pump system of the invention. The system shown in FIG. 3 is a stand-alone system with two membrane diaphragm pumps, which may comprise single-use materials, the operating actions being by pneumatics, which may be from absolute pressure to over atmospheric pressure, the pump being micro processor controlled with various sensors and principles, and in its most simple form with electronically controlled valves, which may be tube sleeve valves, in the fluid stream. Two individual pumps 30, 300 are assembled with back to back for compactness.

Gas pressure on the drive sides 31b, 311b of the diaphragm 31, 311 is regulated by proportional valves. Absolute pressure sensors may measure in real-time the actual gas pressure in both drive chambers 31b, 311b, and fluid in fluid chambers 31a, 311a may be forced in direction according to programming. The position of each diaphragm 31, 311 is measured by a corresponding displacement sensor 34, 344 and information from the displacement sensor is used by the control circuitry, including a micro processor, 115b in FIG. 11, to adjust/correct the reciprocating diaphragm membranes 31, 311 individual position in real-time. Each control unit house may contain a vacuum ejector (not visible) operating on pressurized air also for vacuum generation. The pumps need electrical power for operation supplied by batteries or from mains supply. The on-line communication with the pump may be via wire or wireless.

The two identical pump embodiments, 30, 300 are facing control side towards each other and the diaphragm side facing outwards. In total eight active media valves 32a, 32b, 320a, 320b (four shown) in the fluid stream are connected in two sets of each four to the two control units for pneumatic operation. Valves may take any function (open or closed) according to need and not being specifically passive check valves, but proportional controllable valves, which may be fully independent of fluid mass flow, fluid direction and of each other.

Figure 7:
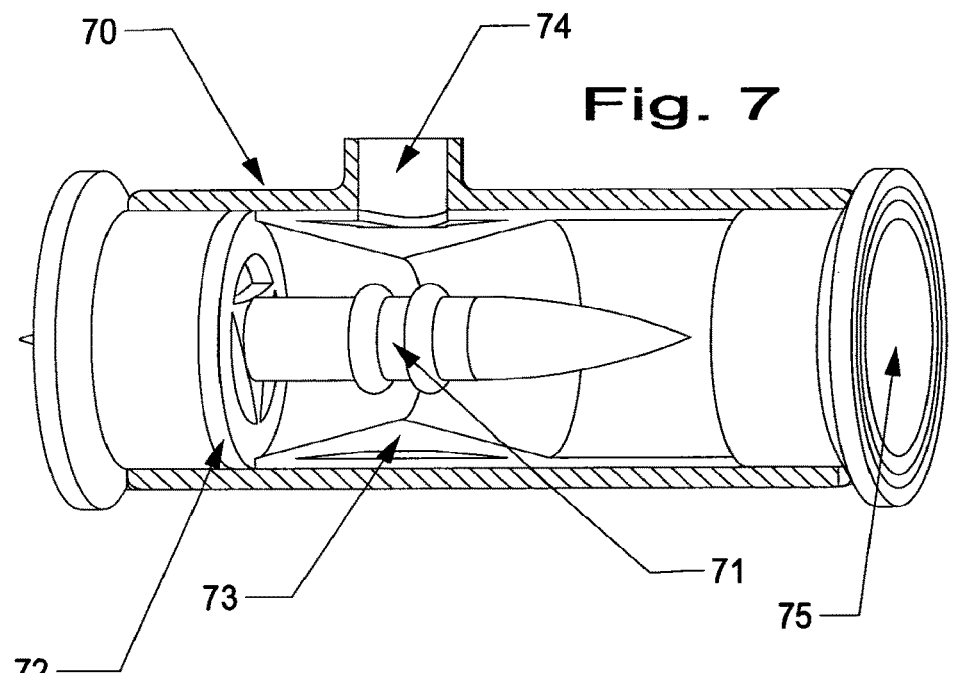
FIG. 7 shows a perspective look of a first embodiment of a sleeve valve assembly according to the invention.
Figure 8:
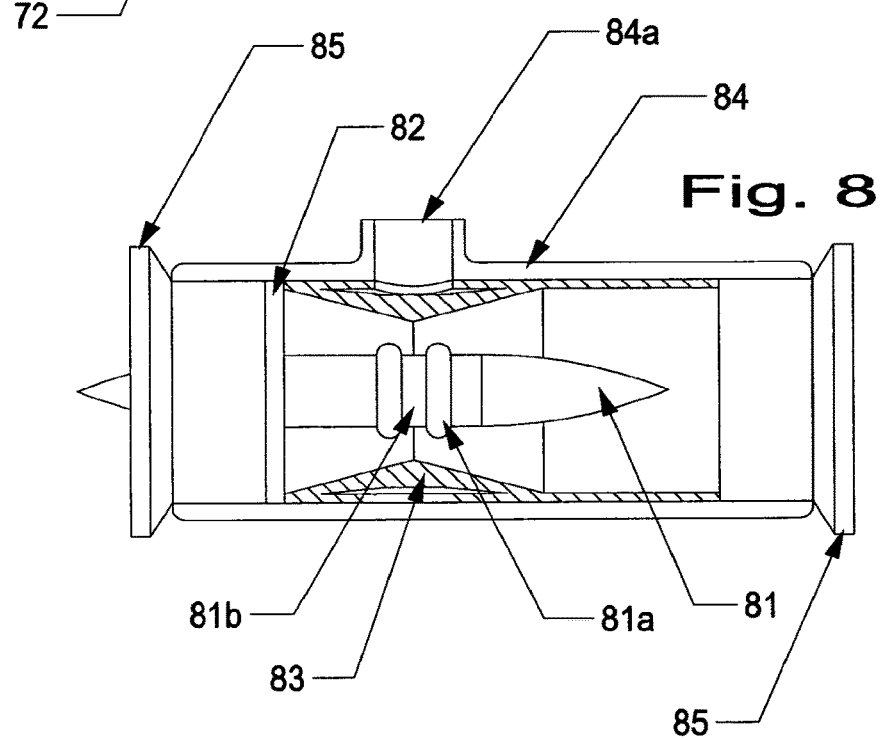
FIG. 8 is a cut view of the sleeve valve of FIG. 7.

The pump system facilitates the control of two independent external fluid circuits via the two port 38a, 38b at top and two ports 38c, 38d at bottom (38d not shown). Any of the four ports may function as either inlet or outlet. Because of the advanced control of each of the twin set of four fluid valves, the pump system is able to drive two individual fluid circuits under different conditions simultaneously. Preferably, the fluid valve bodies are as seen in FIGS. 7 and 8. Like if valve 32a is open, and valves 32b, 320a are closed, then pump 30 will be operational and under deflation of membrane 31 create low pressure in chamber 31a and fluid will run through port 38c into chamber 31a.

Figure 4:
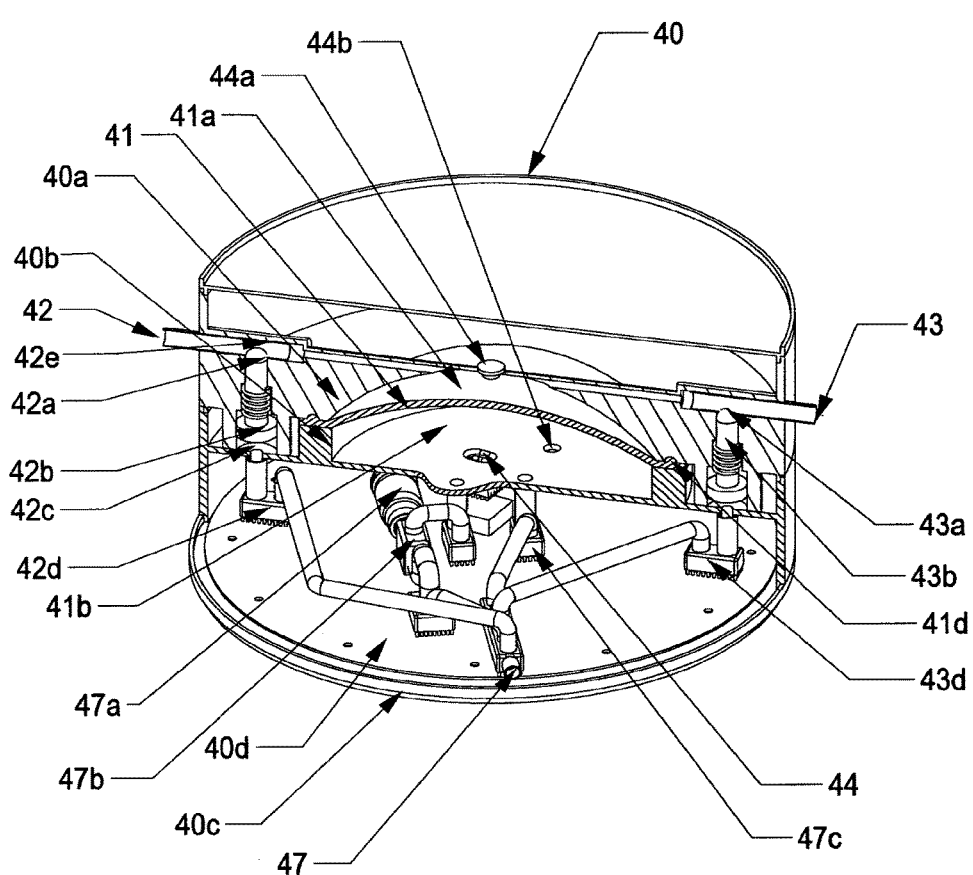
FIG. 4 shows a fourth embodiment of a diaphragm pump system according to the invention, where the system comprises a single diaphragm pump.

FIG. 4 shows a fourth embodiment of a pump system according to the invention. FIG. 4 gives a detailed presentation of a single membrane diaphragm pump 40, which may be integrated with a bioreactor device, a purification device or other devices into a stand-alone unit. The pump 40 consists in general of the following parts:
1. Membrane, diaphragm 41—which may be of disposable capability.
2. Upper house part 40a, defining the fluid chamber 41a with two fluid connections 42, 43 from two fluid valve assemblies 42a, 43a—which may be of disposable capability.
3. Bottom part 40b, defining drive gas chamber 41b under the diaphragm 41—the bottom part 40b may be of disposable capability.
4. Bottom cover 40c, with support for the circuit board 40d with external tube connection 47 for pressurized drive gas distribution among the various pneumatic components.
5. Circuit board 40d attached to the bottom cover 40c.

All the five housing parts when assembled should fulfil the expectation to the functionality of a pump according to the invention. The bottom cover 40c with circuit board 40d, sensors and actuators may be designed to be of reusable capability.
1. The elastic diaphragm 41 is rotational symmetrical and has on the circumference edge a feature for sealing 41d purposes. Further, on the drive side 41b of diaphragm 41, there is a displacement reading window, whereby the displacement sensor 44 is able to measure the distance to and the position of the membrane 41 in real-time.
2. For the upper house part 40a, the fluid chamber 41b is in contact with the media/fluid to be pumped, and the upper house part 40a is able to handle sterilization. Upper house part 40a includes external fluid connections 42, 43. Sensor 44a may measure fluid pressure and temperature in real-time.
3. Bottom part 40b, which include the drive gas chamber 41b, has a gas tight support of the membrane circumference 41d and access ports for: 1. Drive gas, 2. Displacement sensor 44, 3. Pressure sensor 44a. The guillotine designed actuated valves 42a, 43a are controlled by the micro processor of the control circuitry and acts by collapsing a flexible hose or releasing pressure, thereby opening the hose. The guillotine cylinder integrated in the housing facilitates the piston 42b, 43b of relative small diameter with gas pressure on one side 42c and the return spring on the other side of the piston 42b, 43b from on/off valve 42d, 43d. The piston 42b compress the spring and moves under pressure the rod, which forces the rod blade towards the hose 42e oriented safely in a groove of same width as the hose 42e diameter. Bottom cover part 40c has mechanical provision to support the circuit board 40d and provisions for an external set of feet to give the set-up a stable operation like on a bench top.
4. The circuit board integrates electrical provisions for: the displacement sensor 44 seen through its rigid window, drive gas absolute pressure sensor with pressure sensor window 44b, media pressure sensor 44a, temperature sensor, proportional valve 47c, vacuum ejector 47a with its exhaust gas noise silencer, two guillotine valve actuators 42d, 43d, micro processor, plug for a PLC connection, etc.

Figure 5:
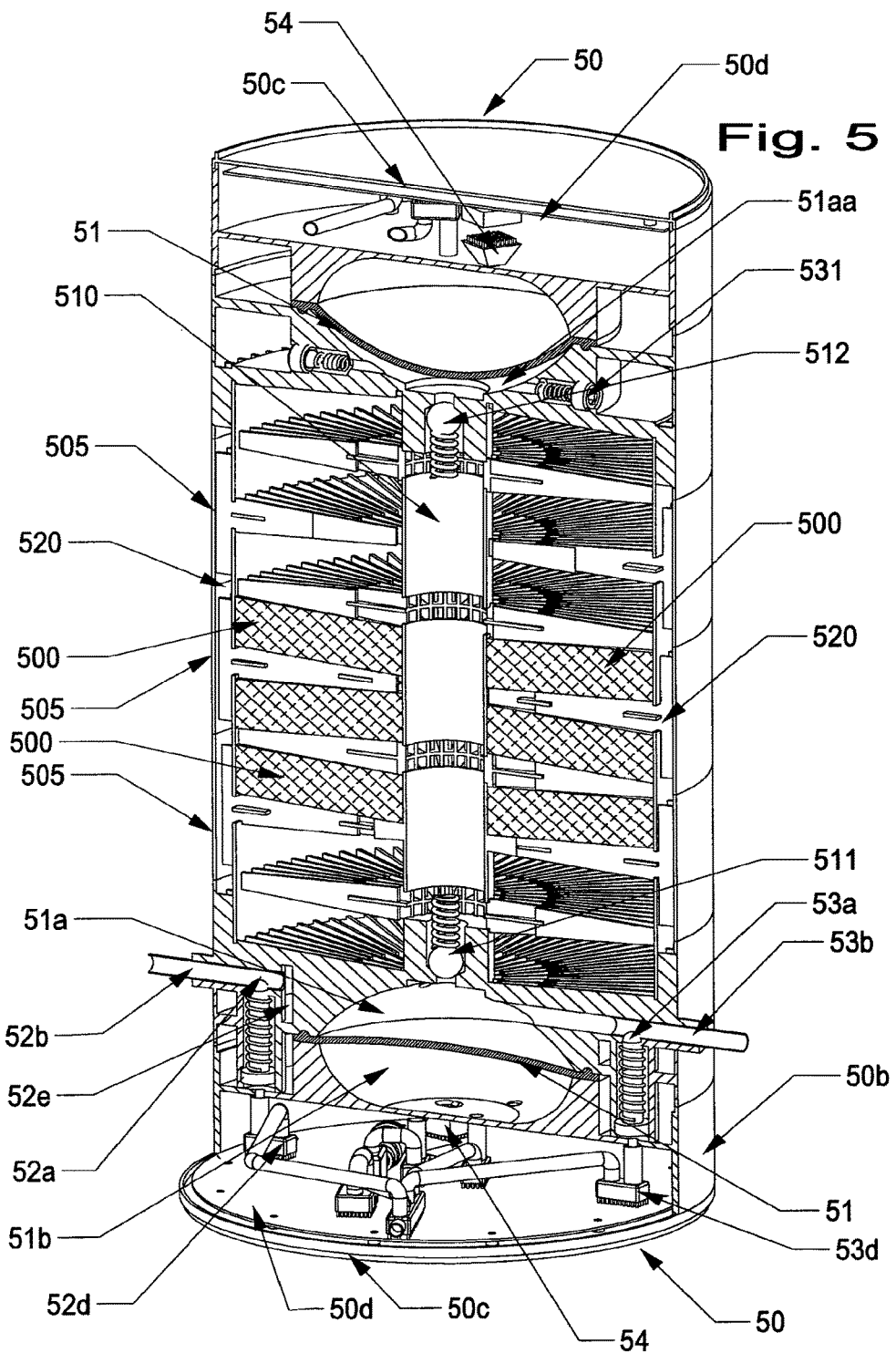
FIG. 5 shows an embodiment of a bioreactor system according to the invention, where the system comprises two diaphragm pumps and a bioreactor.

When the invented pump 40 is integrated with a bioreactor (such as illustrated in FIG. 5) or other devices, the flow path may be guided by two axial mounted passive, spring loaded ball valves with opposite flow direction. The check valves insure the primary fluid flow is through the matrix of the bioreactor. Proportional valves 112b, 112g (see FIG. 11) may supply a pneumatic signal 0-defined pressure relative to the control signal of 0-10 VDC from the micro processor 115b (see FIG. 11).

FIG. 5 shows an embodiment of a bioreactor system, where the system comprises two diaphragm pumps according to the invention. The bioreactor system of FIG. 5 is an example of practical use of two diaphragm pumps 50 of the invention, now combined with a bench-top size eight piece matrix disc 500 (three discs shown) bioreactor, which may be a CerCore bioreactor, the individual parts assembled into one unit integrating:
1. Two pump modules 50 (lower and upper) oriented in opposite direction. The pump modules 50 may comprise disposable parts.
2. Two re-usable control device end covers 50c including a printed circuit board, PCB, 50d.
3. A three module 505 disposable bioreactor oriented in between the pump modules 50.

All three parts may be attached to each other with guides to control the physical rotational correct attachment, thereby creating a bioreactor with media/fluid pumps all integrated inside a housing sharing the same overall dimension—in this example Ø142 mm. An assembled rigid, plastic container including both the bioreactor and two pneumatic driven single-diaphragm 51 pumps 50, which pumps 50 are end-face integrated for operation with fluid conveying channels. The pumps 50 have external corresponding valves 52a, 53a and four check valves 531 for re-circulation, and two check valves 511, 512 in direct connection with the eight cylindrical matrix discs 500 of the bioreactor. The invented set-up benefits from the ability to circulate fluids both internal as well as external, hereby eliminating the need of external traditional peristaltic pumps, and further benefits from being of mainly single-use capability, delivered pre-sterilized and ready to use—including the pumps.

The present example show one pump 50 unit integrated below the bioreactor and one pump unit 50 above the bioreactor, so the matrix centre sees the mass flow from both the bottom and top to the reactor common feed volume 510 and conveyed through the matrix 500. The interaction of the pumps 50, 50 and valves 511, 512 and the four check valves 531 insure the media/fluid is circulating in vortexes radial around the matrix central axis 510 either in perfusion or cross-flow mode along the circumference collection volume 520. The two check valve locations 511, 512 insure one way fluid introduction from each pump.

The two mechanical guillotine type fluid valves 52a, 53a are spring loaded and each individually actuated linear by pilot pneumatics from on/off pneumatic valves (integrated on the circuit board), which on/off valves are controlled by the micro processor and acts by collapsing (closing) the flexible hose 52b, 53b or eliminating the collapsing (opening) of said hose, integrated on the pump housing structure.
1. Fluid flow in path ONE is: media in pump fluid volume 51a is pumped through valve 511 to collection volume 510, forces through the eight matrix discs 500 to the circular collection volume 520, passing the collection volume 520 and conveyed to upper collection volume passing four check valves 531 to pump volume 51aa, forced down through the upper check valve 512 repeating the process again.
2. Fluid flow in path TWO is: fresh media intake channel 53 conveys fresh media to pump volume 51a when bottom diaphragm 51 is deflated into volume 51b and upper diaphragm 51 is kept at constant position.

3. Fluid flow in path THREE is: upper pump 50 force used media down through valve 512 through the matrix 500 which after the matrix pass now containing product flow through lower exit volume 52*e* passing outlet valve 52*a* and outlet 52.

As to the complete control of the invented combined bioreactor/pump, at least the three described flow routines in any such combination are possible.

Figure 6:
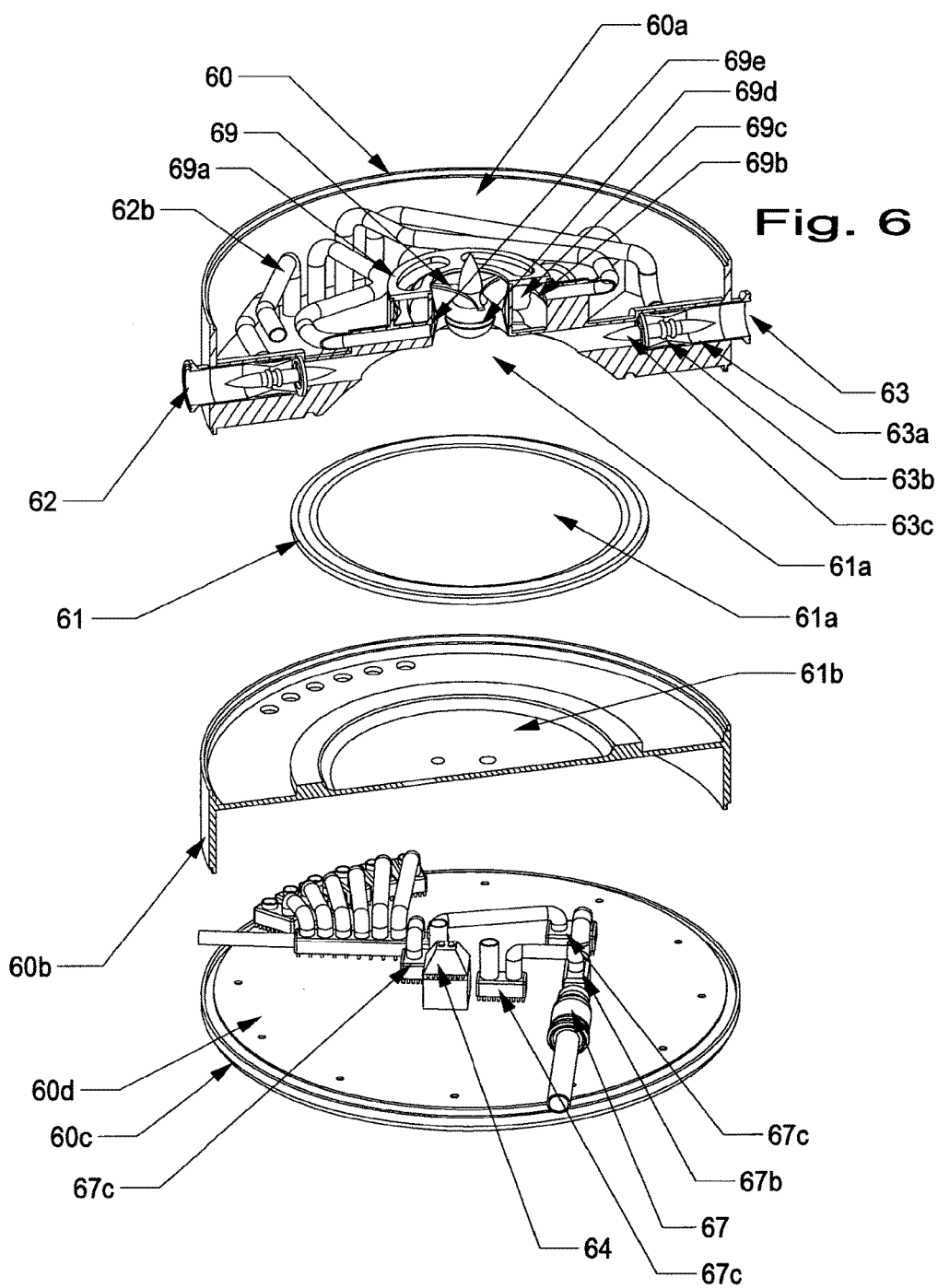
FIG. 6 shows a fifth embodiment of a diaphragm pump system according to the invention, where the system comprises a single diaphragm pumps.

FIG. 6 shows a fifth embodiment of a diaphragm pump of the invention. The pump is a reciprocating diaphragm pump, which may comprise single-use materials, and which has a single diaphragm. The pump may be operating from absolute pressure to over atmospheric pressure, and be electronically controlled by a micro processor connected to various sensors and pneumatics operated valves also in the fluid streams.

The pump of FIG. 6 may easily be integrated with and operate with a bioreactor, such as the new CerCore bioreactor capsules, or may be combined with existing single-use purification capsules (like STAX from Pall) already in use within the pharmaceutical industry. Or the pump may be combined both with a bioreactor, such as the CerCore reactor, and one or more individually specialized purification capsules.

The pump of FIG. 6 may primarily be made of disposable materials, and the following parts may be made of disposable materials:
1. Rigid upper housing part 60*a* with four external media clamp connector flanges.
2. Rigid lower housing part 60*b*.
3. At least one flexible diaphragm 61.
4. Four circumference tube sleeve valves of which 62*a* and 63*a* are visible.
5. One set of end-face mounted sleeve rubber body valves 69.
6. Fluid control devices such as actuators for valves on PCB 60*d*.

Control capsule cover 60*c* may hold the following non disposable parts:
1. Control circuitry including micro processor and general electronics.
2. Sensors and their electronic interface.
3. Pneumatic valves for control of six sleeve valves invisible under cover.
4. Proportional pneumatic valves 67*c*, 67*c*.
5. Vacuum ejector pump 67.
6. Connection for external supply of pressurized air, power supply and control interface.

The pump capsule shell 60*a* is a disposable housing parts manufactured from plastics. The pump capsules has at least one circular end-face fluid connection 69 with dimensions according to the purification capsules standard including both inlet and outlet. Further at least one valve 62*a*, 63*a* (for the pump of FIG. 6 a total of four valves) communicate with external fluid connecting point, in order to facilitate inlet and outlet needs.

As to the advantage of direct communication with purification and/or other modules an axial dual valve set-up 69 is integrated into the upper capsule end face. The centre ring valve parts 69*b*, 69*c* opens or closes for fluid access from the connected unit to pump volume 61*a*. The centre valve parts 69*d*, 69*e* insure closing and opening from fluid volume 61*a* according to needs by pneumatic force conveyed through one of seven visible hoses 62*b* with controlled pressurized air.

The upper housing part 60*a* has a central valve embodiment 69 and at least one valve embodiment 62*a*, 63*a* pointing perpendicular of the central axis from the concave pumping chamber 61*a* to the circumference of the upper housing part 60*a* for external fluid communication. The valve bodies are elastic tube sleeves 63*b*, which may be inflated by pneumatic pressure added to outer side of the tube sleeve, thereby forcing the tube to collapse around a central core part 63*c* locking for any fluid flow through the valve.

The lower housing part 60*b* supports mechanically the diaphragm 61, during maximum inflation with the concave upper housing part 60*a*, and with the lower housing part 60*b* for deflation. The lower housing part further facilitates support for at least one displacement sensor 64, pressure sensor(s), and temperature sensor. Displacement sensor 64 may be based on laser principles and is able to measure the distance to and the position of the membrane 61, and the absolute pressure sensors may be based on micro electronics, and have a flexible transparent window on the wall in order to separate the pressure sensors from the fluid of the fluid volume 61*a*.

The control capsule 60*c* may on the circuit board 60*d* contain the entire package of electronics, sensors and controls. Proportional valve(s) 67*c* for diaphragm control, on/off valves for the tube sleeve valves, and micro processor including control signal connections for the driving gas inlet/outlet on the circumference.

FIG. 7 shows a first embodiment of a sleeve valve assembly according to the invention. The sleeve valve assembly of FIG. 7 facilitates a stand-alone pneumatic operated valve, which may be disposable and manufactured from plastics and elastomers only. The valve 70 is of rotational symmetrical design with a central axis being an elongated core 71, named the torpedo, attached to a perforated plate 72. The valve body is an elastic and expansible tube sleeve 73, which may be inflated by pneumatic pilot pressure through a gas connection port 74 added to radial slot of the tube sleeve 73. The gas pressure forces the tube sleeve 73 to expand inwards to a smaller inner diameter and partially collapse around central core part 71, thereby locking/closing for any fluid flow through the valve 70. The valve 70 has a fluid port 75 in each end, and the ports 75 can take a fluid flow in any direction, thereby acting as both inlet or outlet fluid ports. FIG. 8 is a cut view of the sleeve valve assembly of FIG. 7. The valve 80 of FIG. 8 is assembled from 5 different parts being:
1. A central circular core 81 with radial notches 81*a* and a radial groove 81*b* aligned for the top of the sleeve 83.
2. core washer alike support 82 with (three spokes not visible).
3. An elastomeric sleeve 83 of triangular shape.
4. An outer housing 84 with port 84*a* for pneumatics connection.
5. Two identical sizes and design tri-clamp fittings 85.

The entire valve and all the parts are of disposable capability. Suitable for single-use also with only one tri-clamp 85 and no housing 84 but integrated within the pump upper housing part 60*a* in FIG. 6.

FIG. 9 is a perspective view of a second embodiment of a sleeve valve assembly according to the invention. The assembly of FIG. 9 has two expansible tube sleeve valves integrated into the same dual valve body 69 seen in perspective and cut out of FIG. 6 and enlarged. Each expansive elastomeric element 91*a*, 91*b* is operated from external sources by pneumatics, independent of each other, and convey fluids through the centre port of the four circumference ports of the connection flange 95. When both expansive elastomeric element 91a, 91b are deflated, then both valves are open.

Outer valve, or large circumference valve: Channel 94b from external controlled source supply pressurized air to circular chamber 93bb inside housing circle and inside room in half height elastomeric element 93b. Expansive element 93b seal when pressurised in circular groove 91bb opposite on ring shaped body 91b attached to part of housing surrounding the inner valve.

Inner valve or small centre valve: Channel 94a passing through spoke, for reduced effect on the cross section, from external controlled source supply pressurized air to circular chamber 93aa inside housing circle and inside air room in full height elastomeric element 93a. Expansive element 93a seal when pressurised in circular groove 91aa opposite on drop shaped body 91a attached to part of housing with three spokes 92. Diaphragm membrane 97 of the pump FIG. 6 is seen under the valve body 91a.

FIG. 10 is a cut view of the valve assembly of FIG. 9, with the dual element expansible tube sleeve valve 69 of FIG. 9 seen in a cut view divided with dashed line into a right side and a left side for illustrative purposes.

Left side shows open valves with expansive elements 103b relaxed and in no way exposed to pressurized air or sealing to ring body 101b. Channel 104b conveys pressurised air for expansion or release air for deflation.

Right side shows both valves closed, and centre expansive elements 103a are forced to seal with expansive element edge 103aa against the groove 101aa in adjacent body. Ring shaped valve expansive element 103a is expanded and sealing edge 103aa are forced to grove 101aa on central core 101a.

Figure 11:
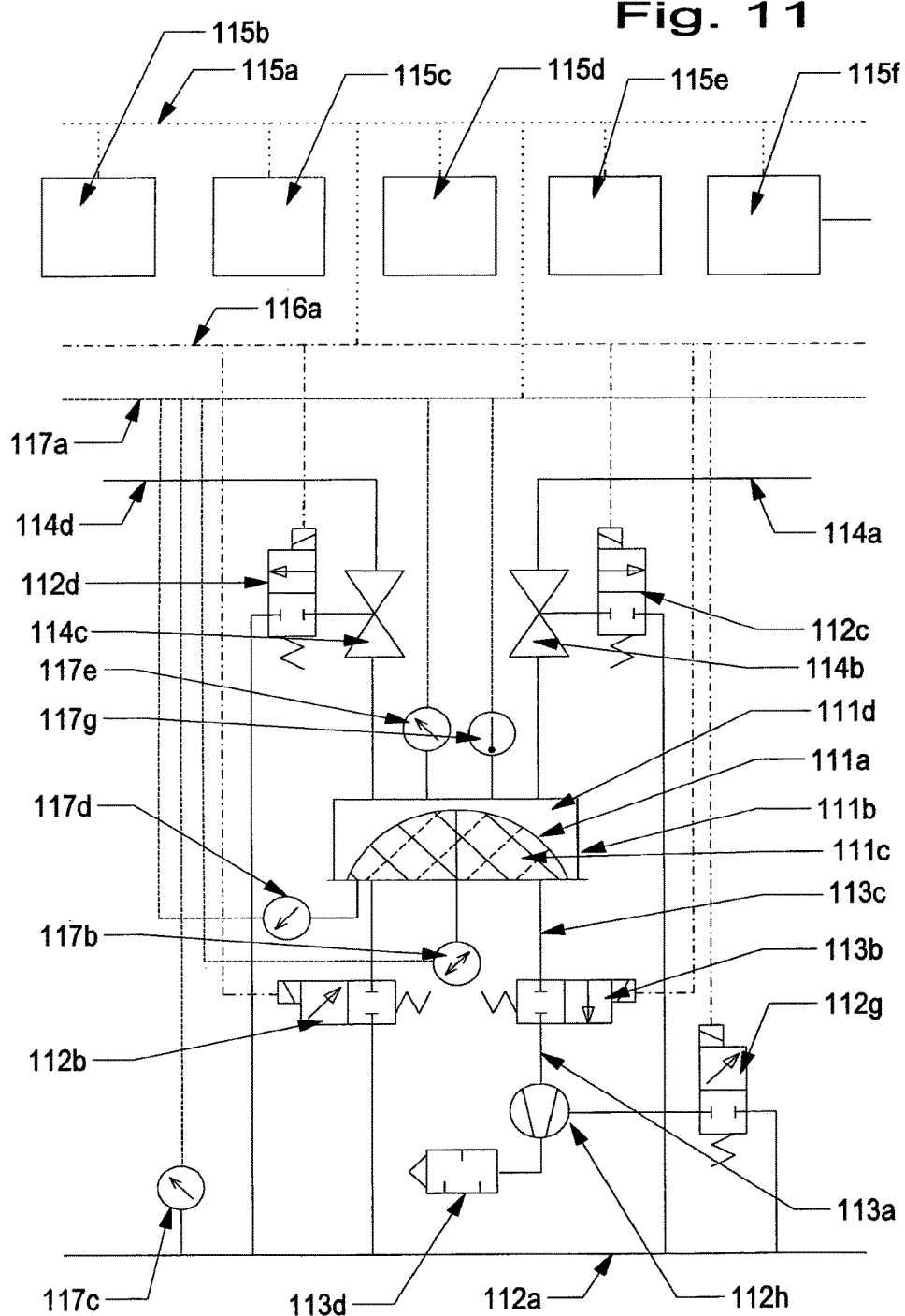
FIG. 11 is a diagram illustrating control devices and control communication lines of a controlled diaphragm pump according to the invention.

FIG. 11 is a diagram illustrating control devices and control communication lines for an electronically controlled diaphragm pump according to the invention. The pump has a diaphragm 111a in a housing 111b with a diaphragm drive 111c, diaphragm fluid side 111d. The operation of the pump is based on:

A pneumatic circuit with supply of pressurized air to a manifold/common bus 112a from the manifold to a proportional valve 112b for control of the diaphragm 111a for inflation, one on/off valve 112c to control the inlet fluid valve 114b, one on/off valve 112d to control the outlet fluid valve 114c, a proportional valve 112g supplying the ejector vacuum pump 112h drive supply inlet, an on/off valve 113b to connect the vacuum injector 112h which supply vacuum to diaphragm drive side 111c deflating diaphragm 111a.

A vacuum circuit to which the vacuum ejector pump 112h suction inlet 113a is connected passing on/off valve 113b further via a tube 113c to the diaphragm drive gas chamber 111c. The exhaust connections on the ejector pump 112h is fitted to the muffler, noise reduction device 113d mounted further with exit to the room air. The vacuum pump 112h is driven through variable pressure supplied by proportional valve 113e supplied from constant pressure from pneumatic manifold 112a.

A fluid circuit with the media/fluid passing inlet entrance 114a, active inlet valve 114b, and the diaphragm 111a fluid side chamber 111d, conveyed under pressure to an active exhaust valve 114c and outlet exit 114d.

An electrical control circuit equipped with a micro processor 115b, a memory device 115c for storing basic operation principles, a memory device 115d for storing individual operation tasks, a communication device 115e for communication with external devices like a PLC via the common internal bus 115a, a power supply 115f to receive external electrical power for drive of the internal components, parts, actuators and sensors.

A control communication bus 116a is connected to proportional valves 112b, 112g and the multiple on/off valves and with internal communication bus 115a.

A sensor circuit with communication bus 117a connected to displacement sensor 117b, pressure sensors 117c, 117d, 117e, and temperature sensors 117g.

Pressure sensor 117c measures the pressure on-line in manifold 112a from external supply, sensor 117d on the drive chamber 111c side, sensor 117e on the fluid chamber 111d side of the diaphragm. Temperature sensor 117g measures the pumped fluid temperature.

The parts of the electrical control circuit may be mounted on a PCB (printed circuit board) housed in a box, and may be house integrated with the pump or be an external mounted box not integrated with the pump, but located at any place with a cable between the control box and the pump.

Figure 12:
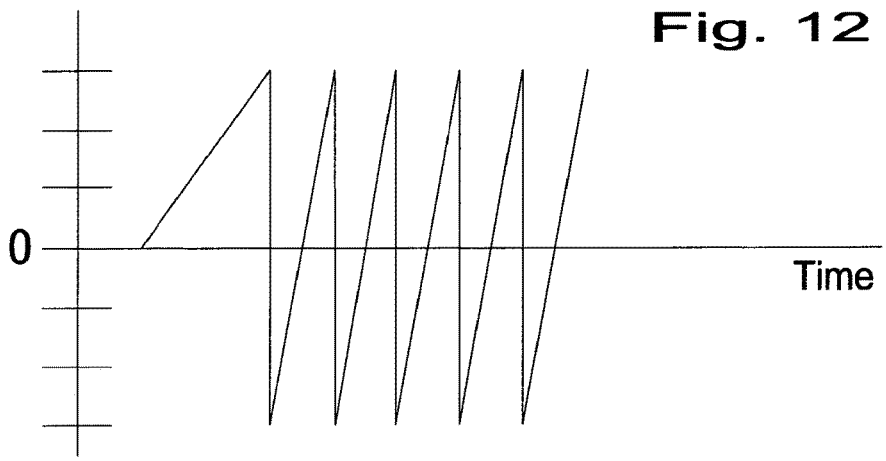
FIG. 12 is a diagram illustrating operation principles for a single diaphragm pump according to an embodiment of the invention where volume control has priority.

FIG. 12 is a diagram illustrating the operation principles for a single diaphragm pump with volume priority as the target. The pump will operate with its maximum pulses and seek to flow a requested volume. The pump will operate between its maximum suction capacity, negative pressure (ranging 90% below atmospheric pressure) capacity and maximum allowed pumping, positive pressure (above atmospheric pressure). In general diaphragm pump are characterised by the strong pulsation effect. With two or more of the invented diaphragm pump working in parallel the pulsation effect is reduced proportionally to the number of units.

Figure 13:
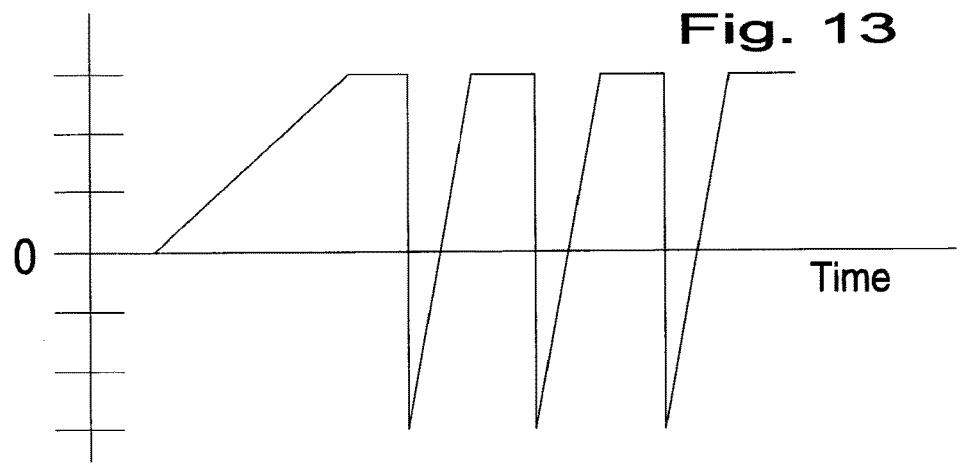
FIG. 13 is a diagram illustrating operation principles for a single diaphragm pump according to an embodiment of the invention where pressure control has priority.

FIG. 13 is a diagram illustrating the operation principles for a single diaphragm pump with pressure priority as the target. Built in pressure sensors give signals to the control unit, which adjusts the drive gas volume and pressure in real-time by use of the proportional valve in order to obtain a maximum pressure. Ramp steepness control at start up with reduced diaphragm velocity, low diaphragm velocity when max pressure is reached, diaphragm return pulsates to lowest possible pressure before a shorter ramp at preset ramp velocity reaches the max pressure and the sequence is repeated. Pressure pulses will be almost eliminated when two pump collaborate like in FIG. 3 and FIG. 5. Both volume and pressure targets may be combined with one selected as the primary measure.

From the above description of the systems of the present invention it is understood that the invention covers pump systems, wherein part of or a major part of the system is made of a disposable material. A large number of disposable materials may be used for this purpose, including organic materials of disposable character taken from the groups: 1. thermo polymers, 2. thermo setting polymers, and 3. elastic polymers.

The controlled fluid conveying valves are illustrated as pneumatic operated valves, but could also be fully electromagnetic controlled.

The systems of the present invention may be useful for operation in conjunction with a bioreactor enclosed in a bag, a vessel, a container for suspension with or without spheres or non floating matrix based bioreactors. The pump may be useful for any application not depending on use within the pharmaceutical industry. In general no airing, exhaust of collected air has been described in any of the description or illustrations. And it should be evident that air pockets will be avoided or de-aired as necessary.

While the present invention has been described in connection with particular embodiments thereof, it will be understood by those skilled in the art that many changes and modifications may be made without departing from the scope of the invention as defined by the appending claims.

What is claimed is:

1. A diaphragm pump for conveying fluids comprising:
   a) a pump housing having a rigid wall comprising a drive gas chamber and a conveyed fluid chamber separated by an independent, free-floating elastic diaphragm membrane, which is in a relaxed state when not in operation;
   wherein the drive gas chamber is connected to at least one drive gas port in said rigid wall, and the at least one drive gas port is adapted to (i) provide controlled drive gas pressure into said drive gas chamber, (ii) suck drive gas out of said drive gas chamber, and/or (iii) release drive gas out of said drive gas chamber;
   wherein the conveyed fluid chamber is connected to at least one fluid inlet port and at least one fluid outlet port in said rigid wall, said at least one fluid inlet port having a fluid inlet valve adapted to open for conveyed fluid inlet when drive gas pressure is reduced in the drive gas chamber or sucked out or released out of the drive gas chamber in relation to atmospheric pressure and at least one fluid outlet port having a fluid outlet valve adapted to open for conveyed fluid outlet when drive gas pressure is higher than atmospheric pressure or increased from reduced or low drive gas pressure in relation to atmospheric pressure in said drive gas chamber;
   b) said elastic diaphragm membrane when forced to expand conveys fluid out of said pump housing through the fluid outlet port and said elastic diaphragm membrane when forced to contract sucks and conveys fluid into said conveyed fluid chamber of the pump housing to fill said conveyed fluid chamber through the fluid inlet port;
   c) wherein the at least one drive gas port is adapted to be connected to a means for providing a drive gas overpressure in relation to atmospheric pressure, in response to a control signal;
   d) wherein the at least one drive gas port is adapted to be connected to a means for providing a drive gas underpressure or suction of drive gas or releasing of drive gas pressure in relation to atmospheric pressure, in response to a control signal;
   e) wherein an exact position of the elastic diaphragm membrane is directly detected in real-time by an optical type or laser type distance sensor; said pump further comprising
   f) a control circuitry equipped (i) with at least one detecting sensor connection connected to the distance sensor, (ii) at least one drive gas proportional regulating valve connected to the drive gas port for in real-time and for dynamically adjusting the position of the elastic diaphragm membrane by regulating in real time said drive gas pressure and (iii) at least one gas pressure sensor for detecting drive gas pressure within the drive gas chamber, wherein the gas pressure sensor delivers a real-time pressure depending signal to the control circuitry.

2. The diaphragm pump according to claim 1, wherein the at least one fluid inlet port and at least one fluid outlet port are the same.

3. The diaphragm pump according to claim 1, wherein the at least one drive gas port in c) and d) are the same.

4. The diaphragm pump according to claim 1, wherein the distance sensor is arranged behind a transparent window provided in the drive gas chamber rigid wall, to thereby permit optical sensing of the distance to the dynamic position of the elastic diaphragm membrane.

5. The diaphragm pump according to claim 1, further comprising at least one pressure sensor for detecting pressure within the conveyed fluid chamber, wherein the fluid pressure sensor delivers a fluid pressure depending signal to the control circuitry.

6. The diaphragm pump according to claim 1, further comprising a temperature sensor for detecting the temperature of the conveyed fluid within the conveyed fluid chamber delivering a fluid temperature depending signal to the control circuitry.

7. The diaphragm pump according to claim 1, wherein the fluid inlet valve and the fluid outlet valve are selected from a group consisting of passive check valves, ball valves, electro mechanical controlled valves, guillotine/pinch valves, sleeve hose valves, diaphragm valves, cross-slit valves, pinch valves and diaphragm valves.

8. The diaphragm pump according to claim 1, wherein the control circuitry and said diaphragm pump is integrated inside the same housing, wherein said control circuitry is able to store a computer program and execute said computer program for controlling the performance of said integrated diaphragm pump.

9. The diaphragm pump according to claim 1, wherein the diaphragm pump is primarily manufactured from disposable materials selected from a list including: thermo polymers, thermo setting plastics, thermo setting polymers and elastic polymers.

* * * * *